United States Patent [19]

Gibbs et al.

[11] Patent Number: 5,519,163

[45] Date of Patent: May 21, 1996

[54] INHIBITORS OF PHOSPHOINOSITIDE-SPECIFIC PHOSPHOLIPASE C

[75] Inventors: Jackson B. Gibbs; Kenneth S. Koblan, both of Chalfont, Pa.; Angus M. MacLeod; Kevin J. Merchant, both of Bishops Stortford, United Kingdom

[73] Assignee: Merck & Co., Inc., Rahway, N.J.

[21] Appl. No.: 138,133

[22] Filed: Oct. 15, 1993

[51] Int. Cl.[6] ............................... C07F 9/38; A61K 31/66
[52] U.S. Cl. .................................................. 562/23
[58] Field of Search ........................ 562/23; 514/130

[56] References Cited

PUBLICATIONS

CA 118:39033t (1992).

Primary Examiner—José G. Dees
Assistant Examiner—Barbara S. Frazier
Attorney, Agent, or Firm—David A. Muthard; Mark R. Daniel

[57] ABSTRACT

Novel α-hydroxyphosphonate compounds which inhibit mammalian phosphoinositide-specific phospholipase-C. The compounds are potent anti-inflammatory and analgesic agents and may be useful for the treatment of cancer.

6 Claims, 11 Drawing Sheets

```
1/1                                              31/11
ATG GCG GGC GCC GCG TCC CCC TGC GCC AAC    GGC TGC GGG CCC AGC GCG CCC TCC GAA GCG
Met ala gly ala ala ser pro cys ala asn    gly cys gly pro ser ala pro ser glu ala
61/21                                            91/31
GAG GTG CTG CAC CTC TGC CGC AGC CTC GAG    GTG GGC ACC GTC ATG ACT TTG TTC TAC TCC
glu val leu his leu cys arg ser leu glu    val gly thr val met thr leu phe tyr ser
121/41                                           151/51
AAG AAG TCG CAG CGG CCA GAA CGG AAG ACC    TTC CAG GTC AAG TTG GAG ACG CGC CAG ATC
lys lys ser gln arg pro glu arg lys thr    phe gln val lys leu glu thr arg gln ile
181/61                                           211/71
ACA TGG AGC CGC GGT GCG GAC AAA ATC GAG    GGG TCC ATC GAT ATC CGA GAA ATC AAG GAG
thr trp ser arg gly ala asp lys ile glu    gly ser ile asp ile arg glu ile lys glu
241/81                                           271/91
ATC CGC CCA GGG AAG ACT TCC CGG GAC TTT    GAC CGC TAC CAA GAA GAC CCT GCC TTC CGG
ile arg pro gly lys thr ser arg asp phe    asp arg tyr gln glu asp pro ala phe arg
301/101                                          331/111
CCA GAT CAG TCA CAC TGT TTT GTC ATC CTC    TAT GGA ATG GAA TTC CGC CTG AAG ACC CTG
pro asp gln ser his cys phe val ile leu    tyr gly met glu phe arg leu lys thr leu
361/121                                          391/131
AGC CTG CAA GCC ACA TCT GAG GAT GAA GTG    AAC ATG TGG ATC AAG GGC TTA ACT TGG CTC
ser leu gln ala thr ser glu asp glu val    asn met trp ile lys gly leu thr trp leu
421/141                                          451/151
ATG GAA GAT ACG CTG CAG GCC GCC ACA CCC    CTG CAA ATT GAG AGA TGG CTC CGG AAG CAG
met glu asp thr leu gln ala ala thr pro    leu gln ile glu arg trp leu arg lys gln
481/161                                          511/171
TTC TAC TCA GTG GAT CGT AAC CGA GAG GAT    CGT ATA TCA GCC AAG GAC CTG AAG AAC ATG
phe tyr ser val asp arg asn arg glu asp    arg ile ser ala lys asp leu lys asn met
541/181                                          571/191
CTG TCA CAG GTC AAC TAC CGG GTC CCC AAC    ATG CGC TTC CTC CGA GAG CGG CTG ACG GAC
leu ser gln val asn tyr arg val pro asn    met arg phe leu arg glu arg leu thr asp
601/201                                          631/211
TTT GAA CAG CGC AGC GGG GAC ATC ACC TAT    GGG CAG TTT GCT CAG CTT TAC CGC AGC CTC
phe glu gln arg ser gly asp ile thr tyr    gly gln phe ala gln leu tyr arg ser leu
661/221                                          691/231
ATG TAC AGC GCC CAG AAG ACG ATG GAC CTT    CCG TTC TTG GAA ACC AAC ACT TTG AGG ACT
met tyr ser ala gln lys thr met asp leu    pro phe leu glu thr asn thr leu arg thr
721/241                                          751/251
GGA GAG CGG CCA GAG CTT TGC CAG GTG TCC    CTT TCT GAG TTC CAG CAG TTC CTT CTT GAG
gly glu arg pro glu leu cys gln val ser    leu ser glu phe gln gln phe leu leu glu
```

FIG.2A

```
781/261                                   811/271
TAC CAG GGG GAG CTG TGG GCT GTC GAC CGG  CTT CAG GTG CAG GAA TTT ATG CTC AGC TTC
tyr gln gly glu leu trp ala val asp arg  leu gln val gln glu phe met leu ser phe
841/281                                   871/291
CTT CGA GAC CCC TTG CGA GAG ATT GAG GAG  CCA TAC TTC TTC TTG GAT GAG CTT GTC ACC
leu arg asp pro leu arg glu ile glu glu  pro tyr phe phe leu asp glu leu val thr
901/301                                   931/311
TTT CTG TTC TCC AAA GAG AAC AGT GTG TGG  AAC TCA CAG CTG GAT GCC GTG TGC CCA GAA
phe leu phe ser lys glu asn ser val trp  asn ser gln leu asp ala val cys pro glu
961/321                                   991/331
ACC ATG AAC AAC CCA CTG TCT CAC TAT TGG  ATC TCT TCC TCG CAT AAT ACG TAT CTG ACT
thr met asn asn pro leu ser his tyr trp  ile ser ser ser his asn thr tyr leu thr
1021/341                                  1051/351
GGG GAC CAG TTC TCC AGC GAG TCC TCC CTG  GAA GCC TAC GCT CGC TGC CTG AGG ATG GGC
gly asp gln phe ser ser glu ser ser leu  glu ala tyr ala arg cys leu arg met gly
1081/361                                  1111/371
TGT CGC TGC ATC GAG TTG GAC TGC TGG GAT  GGG CCA GAT GGG ATG CCA GTC ATT TAC CAT
cys arg cys ile glu leu asp cys trp asp  gly pro asp gly met pro val ile tyr his
1141/381                                  1171/391
GGG CAC ACC CTC ACC ACC AAG ATT AAG TTC  TCA GAT GTC CTG CAC ACC ATC AAG GAG CAC
gly his thr leu thr thr lys ile lys phe  ser asp val leu his thr ile lys glu his
1201/401                                  1231/411
GCG TTC GTA GCC TCA GAG TAC CCT GTC ATC  CTG TCC ATC GAG GAC CAC TGC AGC ATT GCC
ala phe val ala ser glu tyr pro val ile  leu ser ile glu asp his cys ser ile ala
1261/421                                  1291/431
CAG CAG AGG AAC ATG GCC CAG CAC TTC AGG  AAG GTG CTC GGT GAC ACG CTC CTC ACC AAG
gln gln arg asn met ala gln his phe arg  lys val leu gly asp thr leu leu thr lys
1321/441                                  1351/451
CCC GTG GAC ATT GCC GCT GAT GGG CTC CCT  TCT CCC AAC CAG CTC AAG AGG AAG ATC CTG
pro val asp ile ala ala asp gly leu pro  ser pro asn gln leu lys arg lys ile leu
1381/461                                  1411/471
ATT AAG CAT AAG AAG CTG GCT GAG GGC AGT  GCC TAT GAG GAG GTG CCT ACC TCT GTG ATG
ile lys his lys lys leu ala glu gly ser  ala tyr glu glu val pro thr ser val met
1441/481                                  1471/491
TAC TCT GAG AAT GAC ATC AGT AAC TCC ATC  AAG AAT GGT ATC CTC TAC TTG GAG GAC CCC
tyr ser glu asn asp ile ser asn ser ile  lys asn gly ile leu tyr leu glu asp pro
1501/501                                  1531/511
GTG AAT CAT GAG TGC TAC CCC CAC TAC TTT  GTT CTG ACT AGC AGC AAG ATC TAC TAC TCT
val asn his glu trp tyr pro his tyr phe  val leu thr ser ser lys ile tyr tyr ser
```

FIG.2B

```
1561/521                                1591/531
GAG GAG ACC AGC AGT GAC CAG GGA AAT GAG GAT GAA GAG GAG CCG AAG GAG GCC AGT GGC
glu glu thr ser ser asp gln gly asn glu asp glu glu glu pro lys glu ala ser gly
1621/541                                1651/551
AGC ACA GAG CTG CAC TCG AGC GAG AAG TGG TTC CAC GGG AAG CTC GGG GCT GGG CGC GAC
ser thr glu leu his ser ser glu lys trp phe his gly lys leu gly ala gly arg asp
1681/561                                1711/571
GGG CGG CAC ATT GCT GAG CGC CTG CTC ACC GAG TAC TGC ATA GAG ACT GGG GCT CCC GAT
gly arg his ile ala glu arg leu leu thr glu tyr cys ile glu thr gly ala pro asp
1741/581                                1771/591
GGC TCC TTC CTA GTG CGA GAA AGT GAG ACC TTC GTG GGG GAC TAC ACG CTG TCT TTT TGG
gly ser phe leu val arg glu ser glu thr phe val gly asp tyr thr leu ser phe trp
1801/601                                1831/611
CGG AAT GGG AAA GTC CAG CAC TGC CGT ATC CAC TCC CGG CAG GAT GCT GGG ACT CCT AAG
arg asn gly lys val gln his cys arg ile his ser arg gln asp ala gly thr pro lys
1861/621                                1891/631
TTC TTC TTG ACA GAT AAC CTT GTC TTT GAC TCT CTC TAT GAC CTC ATC ACA CAT TAT CAG
phe phe leu thr asp asn leu val phe asp ser leu tyr asp leu ile thr his tyr gln
1921/641                                1951/651
CAA GTG CCC CTG CGC TGC AAT GAG TTT GAG ATG CGC CTT TCA GAG CCT GTT CCA CAG ACG
gln val pro leu arg cys asn glu phe glu met arg leu ser glu pro val pro gln thr
1981/661                                2011/671
AAT GCC CAT GAG AGC AAA GAG TGG TAC CAC GCA AGC CTG ACT AGA GCT CAG GCT GAA CAC
asn ala his glu ser lys glu trp tyr his ala ser leu thr arg ala gln ala glu his
2041/681                                2071/691
ATG CTG ATG CGA GTA CCC CGT GAT GGG GCC TTC CTG GTG CGG AAG CGC AAC GAG CCC AAC
met leu met arg val pro arg asp gly ala phe leu val arg lys arg asn glu pro asn
2101/701                                2131/711
TCC TAT GCC ATC TCT TTC CGG GCT GAG GGA AAG ATC AAG CAC TGC CGA GTA CAG CAG GAA
ser tyr ala ile ser phe arg ala glu gly lys ile lys his cys arg val gln gln glu
2161/721                                2191/731
GGC CAG ACT GTG ATG CTG GGG AAC TCT GAG TTT GAC AGC CTG GTC GAC CTC ATC AGC TAC
gly gln thr val met leu gly asn ser glu phe asp ser leu val asp leu ile ser tyr
2221/741                                2251/751
TAT GAG AAG CAT CCC CTG TAC CGC AAA ATG AAA CTG CGC TAC CCC ATC AAC GAG GAG GCG
tyr glu lys his pro leu tyr arg lys met lys leu arg tyr pro ile asn glu glu ala
2281/761                                2311/771
CTG GAG AAG ATT GGG ACA GCT GAA CCC GAT TAT GGG GCA CTG TAT GAG GGC CGC AAC CCT
leu glu lys ile gly thr ala glu pro asp tyr gly ala leu tyr glu gly arg asn pro
```

FIG.2C

```
2341/781                              2371/791
GGT TTC TAT GTG GAG GCC AAC CCT ATG CCA ACT TTC AAG TGT GCA GTA AAA GCT CTC TTC
gly phe tyr val glu ala asn pro met pro thr phe lys cys ala val lys ala leu phe
2401/801                              2431/811
GAC TAC AAG GCC CAG AGA GAG GAT GAG CTG ACT TTT ACC AAG AGC GCC ATC ATC CAG AAT
asp tyr lys ala gln arg glu asp glu leu thr phe thr lys ser ala ile ile gln asn
2461/821                              2491/831
GTG GAA AAG CAA GAT GGT GGC TGG TGG CGT GGG GAC TAT GGT GGG AAG AAG CAG CTG TGG
val glu lys gln asp gly gly trp trp arg gly asp tyr gly gly lys lys gln leu trp
2521/841                              2551/851
TTC CCC TCA AAC TAT GTG GAA GAG ATG ATC AAT CCA GCA ATC CTA GAG CCG GAG AGG GAG
phe pro ser asn tyr val glu glu met ile asn pro ala ile leu glu pro glu arg glu
2581/861                              2611/871
CAT CTG GAT GAG AAC AGC CCA CTG GGG GAC TTG CTG CGA GGG GTC TTA GAT GTG CCA GCC
his leu asp glu asn ser pro leu gly asp leu leu arg gly val leu asp val pro ala
2641/881                              2671/891
TGC CAG ATC GCC ATT CGT CCT GAG GGC AAA AAC AAC CGG CTC TTC GTC TTC TCC ATC AGC
cys gln ile ala ile arg pro glu gly lys asn asn arg leu phe val phe ser ile ser
2701/901                              2731/911
ATG CCG TCA GTG GCT CAG TGG TCC CTA GAC GTT GCC GCT GAC TCA CAG GAG GAG TTG CAG
met pro ser val ala gln trp ser leu asp val ala ala asp ser gln glu glu leu gln
2761/921                              2791/931
GAC TGG GTG AAA AAG ATC CGT GAA GTT GCC CAG ACT GCA GAT GCC AGG CTT ACT GAG GGG
asp trp val lys lys ile arg glu val ala gln thr ala asp ala arg leu thr glu gly
2821/941                              2851/951
AAG ATG ATG GAG CGG CGG AAG AAG ATC GCC TTG GAG CTC TCC GAG CTC GTG GTC TAC TGC
lys met met glu arg arg lys lys ile ala leu glu leu ser glu leu val val tyr cys
2881/961                              2911/971
CGG CCT GTT CCC TTT GAC GAA GAG AAG ATT GGC ACA GAA CGC GCT TGT TAC CGG GAC ATG
arg pro val pro phe asp glu glu lys ile gly thr glu arg ala  cys tyr arg asp met
2941/981                              2971/991
TCC TCC TTT CCG GAA ACC AAG GCT GAG AAG TAT GTG AAC AAG GCC AAA GGC AAG AAG TTC
ser ser phe pro glu thr lys ala glu lys tyr val asn lys ala lys gly lys lys phe
3001/1001                             3031/1011
CTC CAG TAC AAC CGG CTG CAG CTC TCT CGC ATC TAC CCT AAG GGT CAG AGG CTG GAC TCC
leu gln tyr asn arg leu gln leu ser arg ile tyr pro lys gly gln arg leu asp ser
3061/1021                             3091/1031
TCC AAT TAT GAC CCT CTG CCC ATG TGG ATC TGT GGC AGC CAG CTT GTA GCT CTC AAT TTT
ser asn tyr asp pro leu pro met trp ile cys gly ser gln leu val ala leu asn phe
```

FIG.2D

```
3121/1041                              3151/1051
CAG ACC CCA GAC AAG CCT ATG CAG ATG AAC CAG GCC CTC TTC ATG GCT GGT GGA CAC TGT
gln thr pro asp lys pro met gln met asn gln ala leu phe met ala gly gly his cys
3181/1061                              3211/1071
GGC TAT GTG CTG CAG CCA AGC ACC ATG AGA GAT GAA GCC TTT GAC CCC TTT GAT AAG AGC
gly tyr val leu gln pro ser thr met arg asp glu ala phe asp pro phe asp lys ser
3241/1081                              3271/1091
AGT CTC CGA GGT CTG GAG CCC TGT GTC ATT TGC ATT GAG GTG CTG GGG GCC AGG CAT CTG
ser leu arg gly leu glu pro cys val ile cys ile glu val leu gly ala arg his leu
3301/1101                              3331/1111
CCG AAG AAT GGC CGG GGT ATT GTG TGT CCT TTC GTG GAG ATT GAA GTG GCT GGG GCA GAG
pro lys asn gly arg gly ile val cys pro phe val glu ile glu val ala gly ala glu
3361/1121                              3391/1131
TAC GAC AGC ACC AAG CAG AAG ACA GAG TTT GTA GTG GAC AAT GGA CTG AAC CCT GTG TGG
tyr asp ser thr lys gln lys thr glu phe val val asp asn gly leu asn pro val trp
3421/1141                              3451/1151
CCT GCA AAG CCC TTC CAC TTC CAG ATC AGT AAC CCA GAG TTT GCC TTT CTG CGC TTT GTG
pro ala lys pro phe his phe gln ile ser asn pro glu phe ala phe leu arg phe val
3481/1161                              3511/1171
GTG TAT GAG GAA GAC ATG TTT AGT GAC CAG AAC TTC TTG GCT CAG GCT ACT TTC CCA GTA
val tyr glu glu asp met phe ser asp gln asn phe leu ala gln ala thr phe pro val
3541/1181                              3571/1191
AAA GGC CTG AAG ACA GGA TAC AGA GCA GTG CCT TTG AAG AAC AAC TAC AGT GAA GAC CTG
lys gly leu lys thr gly tyr arg ala val pro leu lys asn asn tyr ser glu asp leu
3601/1201                              3631/1211
GAG TTG GCC TCC CTG CTC ATC AAG ATT GAC ATT TTC CCT GCT AAG GAG AAT GGT GAC CTC
glu leu ala ser leu leu ile lys ile asp ile phe pro ala lys glu asn gly asp leu
3661/1221                              3691/1231
AGC CCT TTC AGT GGT ACA TCC CTA AGG GAA CGG GCC TCA GAT GCC TCC AGC CAG CTG TTC
ser pro phe ser gly thr ser leu arg glu arg ala ser asp ala ser ser gln leu phe
3721/1241                              3751/1251
CAT GTC CGG GCC CGG GAA GGG TCC TTT GAA GCC AGA TAC CAG CAG CCA TTT GAA GAC TTC
his val arg ala arg glu gly ser phe glu ala arg tyr gln gln pro phe glu asp phe
3781/1261                              3811/1271
CGC ATC TCG CAG GAG CAT CTC GCA GAC CAT TTT GAC AGT CGG GAA CGA AGC GCC CCA AGA
arg ile ser gln glu his leu ala asp his phe asp ser arg glu arg arg ala pro arg
3841/1281
AGG ACT CGG GTC AAT GGA GAC AAC CGC CTC
arg thr arg val asn gly asp asn arg leu
```

FIG.2E

```
1/1                                  31/11
ATG GCG GGC GCC GCG TCC CCC TGC GCC AAC   GGC TGC GGG CCC AGC GCG CCC TCC GAA GCG
Met ala gly ala ala ser pro cys ala asn   gly cys gly pro ser ala pro ser glu ala
61/21                                91/31
GAG GTG CTG CAC CTC TGC CGC AGC CTC GAG   GTG GGC ACC GTC ATG ACT TTG TTC TAC TCC
glu val leu his leu cys arg ser leu glu   val gly thr val met thr leu phe tyr ser
121/41                               151/51
AAG AAG TCG CAG CGG CCA GAA CGG AAG ACC   TTC CAG GTC AAG TTG GAG ACG CGC CAG ATC
lys lys ser gln arg pro glu arg lys thr   phe gln val lys leu glu thr arg gln ile
181/61                               211/71
ACA TGG AGC CGC GGT GCG GAC AAA ATC GAG   GGG TCC ATC GAT ATC CGA GAA ATC AAG GAG
thr trp ser arg gly ala asp lys ile glu   gly ser ile asp ile arg glu ile lys glu
241/81                               271/91
ATC CGC CCA GGG AAG ACT TCC CGG GAC TTT   GAC CGC TAC CAA GAA GAC CCT GCC TTC CGG
ile arg pro gly lys thr ser arg asp phe   asp arg tyr gln glu asp pro ala phe arg
301/101                              331/111
CCA GAT CAG TCA CAC TGT TTT GTC ATC CTC   TAT GGA ATG GAA TTC CGC CTG AAG ACC CTG
pro asp gln ser his cys phe val ile leu   tyr gly met glu phe arg leu lys thr leu
361/121                              391/131
AGC CTG CAA GCC ACA TCT GAG GAT GAA GTG   AAC ATG TGG ATC AAG GGC TTA ACT TGG CTC
ser leu gln ala thr ser glu asp glu val   asn met trp ile lys gly leu thr trp leu
421/141                              451/151
ATG GAA GAT ACG CTG CAG GCG GCC ACA CCC   CTG CAA ATT GAG AGA TGG CTC CGG AAG CAG
met glu asp thr leu gln ala ala thr pro   leu gln ile glu arg trp leu arg lys gln
481/161                              511/171
TTC TAC TCA GTG GAT CGT AAC CGA GAG GAT   CGT ATA TCA GCC AAG GAC CTG AAG AAC ATG
phe tyr ser val asp arg asn arg glu asp   arg ile ser ala lys asp leu lys asn met
541/181                              571/191
CTG TCA CAG GTC AAC TAC CGG GTC CCC AAC   ATG CGC TTC CTC CGA GAG CGG CTG ACG GAC
leu ser gln val asn tyr arg val pro asn   met arg phe leu arg glu arg leu thr asp
601/201                              631/211
TTT GAA CAG CGC AGC GGG GAC ATC ACC TAT   GGG CAG TTT GCT CAG CTT TAC CGC AGC CTC
phe glu gln arg ser gly asp ile thr tyr   gly gln phe ala gln leu tyr arg ser leu
661/221                              691/231
ATG TAC AGC GCC CAG AAG ACG ATG GAC CTT   CCG TTC TTG GAA ACC AAC ACT TTG AGG ACT
met tyr ser ala gln lys thr met asp leu   pro phe leu glu thr asn thr leu arg thr
721/241                              751/251
GGA GAG CGG CCA GAG CTT TGC CAG GTG TCC   CTT TCT GAG TTC CAG CAG TTC CTT CTT GAG
gly glu arg pro glu leu cys gln val ser   leu ser glu phe gln gln phe leu leu glu
```

FIG.3A

```
781/261                                      811/271
TAC CAG GGG GAG CTG TGG GCT GTC GAC CGG CTT CAG GTG CAG GAA TTT ATG CTC AGC TTC
tyr gln gly glu leu trp ala val asp arg leu gln val gln glu phe met leu ser phe
841/281                                      871/291
CTT CGA GAC CCC TTG CGA GAG ATT GAG GAG CCA TAC TTC TTC TTG GAT GAG CTT GTC ACC
leu arg asp pro leu arg glu ile glu glu pro tyr phe phe leu asp glu leu val thr
901/301                                      931/311
TTT CTG TTC TCC AAA GAG AAC AGT GTG TGG AAC TCA CAG CTG GAT GCC GTG TGC CCA GAA
phe leu phe ser lys glu asn ser val trp asn ser gln leu asp ala val cys pro glu
961/321                                      991/331
ACC ATG AAC AAC CCA CTG TCT CAC TAT TGG ATC TCT TCC TCG CAT AAT ACG TAT CTG ACT
thr met asn asn pro leu ser his tyr trp ile ser ser ser his asn thr tyr leu thr
1021/341                                     1051/351
GGG GAC CAG TTC TCC AGC GAG TCC TCC CTG GAA GCC TAC GCT CGC TGC CTG AGG ATG GGC
gly asp gln phe ser ser glu ser ser leu glu ala tyr ala arg cys leu arg met gly
1081/361                                     1111/371
TGT CGC TGC ATC GAG TTG GAC TGC TGG GAT GGG CCA GAT GGG ATG CCA GTC ATT TAC CAT
cys arg cys ile glu leu asp cys trp asp gly pro asp gly met pro val ile tyr his
1141/381                                     1171/391
GGG CAC ACC CTC ACC ACC AAG ATT AAG TTC TCA GAT GTC CTG CAC ACC ATC AAG GAG CAC
gly his thr leu thr thr lys ile lys phe ser asp val leu his thr ile lys glu his
1201/401                                     1231/411
GCG TTC GTA GCC TCA GAG TAC CCT GTC ATC CTG TCC ATC GAG GAC CAC TGC AGC ATT GCC
ala phe val ala ser glu tyr pro val ile leu ser ile glu asp his cys ser ile ala
1261/421                                     1291/431
CAG CAG AGG AAC ATG GCC CAG CAC TTC AGG AAG GTG CTC GGT GAC ACG CTC CTC ACC AAG
gln gln arg asn met ala gln his phe arg lys val leu gly asp thr leu leu thr lys
1321/441                                     1351/451
CCC GTG GAC ATT GCC GCT GAT GGG CTC CCT TCT CCC AAC CAG CTC AAG AGG AAG ATC CTG
pro val asp ile ala ala asp gly leu pro ser pro asn gln leu lys arg lys ile leu
1381/461                                     1411/471
ATT AAG CAT AAG AAG CTG GCT GAG GGC AGT GCC TAT GAG GAG GTG CCT ACC TCT GTG ATG
ile lys his lys lys leu ala glu gly ser ala tyr glu glu val pro thr ser val met
1441/481                                     1471/491
TAC TCT GAG AAT GAC ATC AGT AAC TCC ATC AAG AAT GGT ATC CTC TAC TTG GAG GAC CCC
tyr ser glu asn asp ile ser asn ser ile lys asn gly ile leu tyr leu glu asp pro
1501/501                                     1531/511
GTG AAT CAT GAG TGG TAC CCC CAC TAC TTT GTT CTG ACT AGC AGC AAG ATC TAC TAC TCT
val asn his glu trp tyr pro his tyr phe val leu thr ser ser lys ile tyr tyr ser
```

FIG.3B

1561/521
GAG GAG ACC AGC AGT GAC CAG GGA AAT GAG
glu glu thr ser ser asp gln gly asn glu 1591/531
GAT GAA GAG GAG CCC AAG GAG GCC AGT GGC
asp glu glu glu pro lys glu ala ser gly 1621/541
AGC ACA GAG CTG CAC TCG AGC GAG AAG TGG
ser thr glu leu his ser ser glu lys trp 1651/551
TTC CAC GGG AAG CTC GGG GCT GGG CGC GAC
phe his gly lys leu gly ala gly arg asp 1681/561
GGG CGG CAC ATT GCT GAG CGC CTG CTC ACC
gly arg his ile ala glu arg leu leu thr 1711/571
GAG TAC TGC ATA GAG ACT GGG GCT CCC GAT
glu tyr cys ile glu thr gly ala pro asp 1741/581
GGC TCC TTC CTA GTG CGA GAA AGT GAG ACC
gly ser phe leu val arg glu ser glu thr 1771/591
TTC GTG GGG GAC TAC ACG CTG TCT TTT TGG
phe val gly asp tyr thr leu ser phe trp 1801/601
CGG AAT GGG AAA GTC CAG CAC TGC CGT ATC
arg asn gly lys val gln his cys arg ile 1831/611
CAC TCC CGG CAG GAT GCT GGG ACT CCT AAG
his ser arg gln asp ala gly thr pro lys 1861/621
TTC TTC TTG ACA GAT AAC CTT GTC TTT GAC
phe phe leu thr asp asn leu val phe asp 1891/631
TCT CTC TAT GAC CTC ATC ACA CAT TAT CAG
ser leu tyr asp leu ile thr his tyr gln 1921/641
CAA GTG CCC CTG CGC TGC AAT GAG TTT GAG
gln val pro leu arg cys asn glu phe glu 1951/651
ATG CGC CTT TCA GAG CCT GTT CCA CAG ACG
met arg leu ser glu pro val pro gln thr 1981/661
AAT GCC CAT GAG AGC AAA GAG TGG TAC CAC
asn ala his glu ser lys glu trp tyr his 2011/671
GCA AGC CTG ACT AGA GCT CAG GCT GAA CAC
ala ser leu thr arg ala gln ala glu his 2041/681
ATG CTG ATG CGA GTA CCC CGT GAT GGG GCC
met leu met arg val pro arg asp gly ala 2071/691
TTC CTG GTG CGG AAG CGC AAC GAG CCC AAC
phe leu val arg lys arg asn glu pro asn 2101/701
TCC TAT GCC ATC TCT TTC CGG GCT GAG GGA
ser tyr ala ile ser phe arg ala glu gly 2131/711
AAG ATC AAG CAC TGC CGA GTA CAG CAG GAA
lys ile lys his cys arg val gln gln glu 2161/721
GGC CAG ACT GTG ATG CTG GGG AAC TCT GAG
gly gln thr val met leu gly asn ser glu 2191/731
TTT GAC AGC CTG GTC GAC CTC ATC AGC TAC
phe asp ser leu val asp leu ile ser tyr 2221/741
TAT GAG AAG CAT CCC CTG TAC CGC AAA ATG
tyr glu lys his pro leu tyr arg lys met 2251/751
AAA CTG CGC TAC CCC ATC AAC GAG GAG GCG
lys leu arg tyr pro ile asn glu glu ala 2281/761
CTG GAG AAG ATT GGG ACA GCT GAA CCC GAT
leu glu lys ile gly thr ala glu pro asp 2311/771
TAT GGG GCA CTG TAT GAG GGC CGC AAC CCT
tyr gly ala leu tyr glu gly arg asn pro

FIG.3C

```
2341/781                              2371/791
GGT TTC TAT GTG GAG GCC AAC CCT ATG CCA ACT TTC AAG TGT GCA GTA AAA GCT CTC TTC
gly phe tyr val glu ala asn pro met pro thr phe lys cys ala val lys ala leu phe
2401/801                              2431/811
GAC TAC AAG GCC CAG AGA GAG GAT GAG CTG ACT TTT ACC AAG AGC GCC ATC ATC CAG AAT
asp tyr lys ala gln arg glu asp glu leu thr phe thr lys ser ala ile ile gln asn
2461/821                              2491/831
GTG GAA AAG CAA GAT GGT GGC TGG TGG CGT GGG GAC TAT GGT GGG AAG AAG CAG CTG TGG
val glu lys gln asp gly gly trp trp arg gly asp tyr gly gly lys lys gln leu trp
2521/841                              2551/851
TTC CCC TCA AAC TAT GTG GAA GAG ATG ATC AAT CCA GCA ATC CTA GAG CCG GAG AGG GAG
phe pro ser asn tyr val glu glu met ile asn pro ala ile leu glu pro glu arg glu
2581/861                              2611/871
CAT CTG GAT GAG AAC AGC CCA CTG GGG GAC TTG CTG CGA GGG GTC TTA GAT GTG CCA GCC
his leu asp glu asn ser pro leu gly asp leu leu arg gly val leu asp val pro ala
2641/881                              2671/891
TGC CAG ATC GCC ATT CGT CCT GAG GGC AAA AAC AAC CGG CTC TTC GTC TTC TCC ATC AGC
cys gln ile ala ile arg pro glu gly lys asn asn arg leu phe val phe ser ile ser
2701/901                              2731/911
ATG CCG TCA GTG GCT CAG TGG TCC CTA GAC GTT GCC GCT GAC TCA CAG GAG GAG TTG CAG
met pro ser val ala gln trp ser leu asp val ala ala asp ser gln glu glu leu gln
2761/921                              2791/931
GAC TGG GTG AAA AAG ATC CGT GAA GTT GCC CAG ACT GCA GAT GCC AGG CTT ACT GAG GGG
asp trp val lys lys ile arg glu val ala gln thr ala asp ala arg leu thr glu gly
2821/941                              2851/951
AAG ATG ATG GAG cGG cGG AAG AAG ATC GCC TTG GAG CTC TCC GAG CTC GTG GTC TAC TGC
lys met met glu arg arg lys lys ile ala leu glu leu ser glu leu val val tyr cys
2881/961                              2911/971
CGG CCT GTT CCC TTT GAC GAA GAG AAG ATT GGC ACA GAA CGC GCT TGT TAC CGG GAC ATG
arg pro val pro phe asp glu glu lys ile gly thr glu arg ala cys tyr arg asp met
2941/981                              2971/991
TCC TCC TTT CCG GAA ACC AAG GCT GAG AAG TAT GTG AAC AAG GCC AAA GGC AAG AAG TTC
ser ser phe pro glu thr lys ala glu lys tyr val asn lys ala lys gly lys lys phe
3001/1001                             3031/1011
CTC CAG TAC AAC CGG CTG CAG CTC TCT CGC ATC TAC CCT AAG GGT CAG AGG CTG GAC TCC
leu gln tyr asn arg leu gln leu ser arg ile tyr pro lys gly gln arg leu asp ser
3061/1021                             3091/1031
TCC AAT TAT GAC CCT CTG CCC ATG TGG ATC TGT GGC AGC CAG CTT GTA GCT CTC AAT TTT
ser asn tyr asp pro leu pro met trp ile cys gly ser gln leu val ala leu asn phe
```

FIG.3D

```
3121/1041                                    3151/1051
CAG ACC CCA GAC AAG CCT ATG CAG ATG AAC      CAG GCC CTC TTC ATG GCT GGT GGA CAC TGT
gln thr pro asp lys pro met gln met asn      gln ala leu phe met ala gly gly his cys
3181/1061                                    3211/1071
GGC TAT GTG CTG CAG CCA AGC ACC ATG AGA      GAT GAA GCC TTT GAC CCC TTT GAT AAG AGC
gly tyr val leu gln pro ser thr met arg      asp glu ala phe asp pro phe asp lys ser
3241/1081                                    3271/1091
AGT CTC CGA GGT CTG GAG CCC TGT GTC ATT      TGC ATT GAG GTG CTG GGG GCC AGG CAT CTG
ser leu arg gly leu glu pro cys val ile      cys ile glu val leu gly ala arg his leu
3301/1101                                    3331/1111
CCG AAG AAT GGC CGG GGT ATT GTG TGT CCT      TTC GTG GAG ATT GAA GTG GCT GGG GCA GAG
pro lys asn gly arg gly ile val cys pro      phe val glu ile glu val ala gly ala glu
3361/1121                                    3391/1131
TAC GAC AGC ACC AAG CAG AAG ACA GAG TTT      GTA GTG GAC AAT GGA CTG AAC CCT GTG TGG
tyr asp ser thr lys gln lys thr glu phe      val val asp asn gly leu asn pro val trp
3421/1141                                    3451/1151
CCT GCA AAG CCC TTC CAC TTC CAG ATC AGT      AAC CCA GAG TTT GCC TTT CTG CGC TTT GTG
pro ala lys pro phe his phe gln ile ser      asn pro glu phe ala phe leu arg phe val
3481/1161                                    3511/1171
GTG TAT GAG GAA GAC ATG TTT AGT GAC CAG      AAC TTC TTG GCT CAG GCT ACT TTC CCA GTA
val tyr glu glu asp met phe ser asp gln      asn phe leu ala gln ala thr phe pro val
3541/1181                                    3571/1191
AAA GGC CTG AAG ACA GGA TAC AGA GCA GTG      CCT TTG AAG AAC AAC TAC AGT GAA GAC CTG
lys gly leu lys thr gly tyr arg ala val      pro leu lys asn asn tyr ser glu asp leu
3601/1201                                    3631/1211
GAG TTG GCC TCC CTG CTC ATC AAG ATT GAC      ATT TTC CCT GCT AAG GAG AAT GGT GAC CTC
glu leu ala ser leu leu ile lys ile asp      ile phe pro ala lys glu asn gly asp leu
3661/1221                                    3691/1231
AGC CCT TTC AGT GGT ACA TCC CTA AGG GAA      CGG GCC TCA GAT GCC TCC AGC CAG CTG TTC
ser pro phe ser gly thr ser leu arg glu      arg ala ser asp ala ser ser gln leu phe
3721/1241                                    3751/1251
CAT GTC CGG GCC CGG GAA GGG TCC TTT GAA      GCC AGA TAC CAG CAG CCA TTT GAA GAC TTC
his val arg ala arg glu gly ser phe glu      ala arg tyr gln gln pro phe glu asp phe
3781/1261                                    3811/1271
CGC ATC TCG CAG GAG CAT CTC GCA GAC CAT      TTT GAC AGT CGG GAA CGA AGG GCC CCA AGA
arg ile ser gln glu his leu ala asp his      phe asp ser arg glu arg arg ala pro arg
3841/1281                                    3871/1291
AGG ACT CGG GTC AAT GGA GAC AAC CGC CTC      gaa gaa ttt TAG tct agA AGC TT
arg thr arg val asn gly asp asn arg leu      glu glu phe AMB
```

FIG.3E

INHIBITORS OF PHOSPHOINOSITIDE-SPECIFIC PHOSPHOLIPASE C

BACKGROUND OF THE INVENTION

Phospholipases C (EC 3.1.4.3) are a family of enzymes which hydrolyze the sn-3 phosphodiester bond in membrane phospholipids producing diacylglycerol and a phosphorylated polar head group. Mammalian phospholipase C (PLC) enzymes exhibit specificity for the polar head group which is hydrolyzed, i.e., phosphatidylcholine, phosphatidylinositol, etc. Recently, much interest has been generated in those PLC enzymes which selectively hydrolyze phosphoinositide lipids in response to receptor occupancy by agonist. Hydrolysis of phosphatidylinositol 4,5-bisphosphate generates two second messenger molecules; diacylglycerol, a co-factor required for activation of protein kinase C, and inositol 1,4,5-trisphosphate, a soluble second messenger molecule which promotes the release of intracellular non-mitochondrial stores of calcium (Berridge, *Ann. Rev. Biochem.*, 56:159–193, 1987). The diacylglycerol released may be further metabolized to free arachidonic acid by sequential actions of diglycerol lipase and monoglycerol lipase. Thus, phospholipases C are not only important enzymes in the generation of second messenger molecules, but may serve an important role in making arachidonic acid available for eicosanoid biosynthesis in select tissues.

Mammalian tissues contain multiple distinct forms of phosphoinositide-specific PLC (Crooke and Bennett, *Cell Calcium*, 10:309–323, 1989; Rhee et al., *Science*, 244:546–550, 1989). It is proposed that each of the enzymes couple to distinct classes of cell surface receptors, i.e., PLC-$\beta$ couples to thromboxane $A_2$, bradykinin, angiotensin and muscarinic receptors via $G_q\alpha$ or $G_{11}\alpha$ (Shenker et al., *J. Biol. Chem.*, 266:9309–9312 (1991); Gutowski et al., *J. Biol. Chem.*, 266:20519–20524 (1991); Berstein et al., *J. Biol. Chem.*, 267:8081–8088 (1992)), PLC-$\gamma$ couples to growth factor receptors, etc. (Aiyar et al., *Biochem. J.*, 261:63–70, 1989; Crooke and Bennett, *Cell Calcium*, 10:309–323, 1989; Margolis et al., *Cell*, 57:1101–1107, 1989; Wahl et al., *Proc. Natl. Acad. Sci. USA*, 86:1568–1572, 1989). Alignment of sequences from all groups reveals that the most conserved residues are clustered into two distinct regions (one of ~170 amino acids and the other of ~260 amino acids), designated the X and Y regions, respectively. PLC$\gamma_1$ also contains src-homology regions (SH2 and SH3) that appear to mediate the interaction between the enzyme and receptors with tyrosine kinase activity, such as the epidermal growth factor (EGF) receptor (Stahl et al. *Nature*, 332:269–272 (1988); Katan et al., *Cell*, 54:171–177 (1988)).

The PLC isozymes are activated by different mechanisms in response to stimulation of specific cell surface receptors. Coupling of PLC$\delta$ to specific receptors or downstream effectors has not been reported but this isozyme may be associated with mechanisms that regulate the tone of vascular smooth muscle. Activation of PLC$\beta$ is achieved by guanine nucleotide binding proteins of the Gq class.

To date, the cDNA for 6 distinct PI-PLC enzymes have been cloned. The enzymes range in size from 504 amino acids to 1250 amino acids, and are remarkably divergent considering that they exhibit similar biochemical properties. 4 of the 5 enzymes (PLC-$\beta$, PLC-$\delta_1$, PLC-$\delta_2$, and PLC-$\gamma_1$) contain two domains approximately 250 amino acids in length which exhibit between 50 to 80% sequence similarity. The marked differences in DNA sequences for the different PI-PLC enzyme allows the selective targeting of one PI-PLC enzyme, without affecting other enzymes using antisense technology. The human cDNA clone has been reported for PLC-$\delta_2$, (Ohta et al., *FEBS Lett.*, 242:31–35, 1988) and PLC-$\gamma$1 (Burgess et al., *Mol. Cell. Biol.*, 10:4770–4777 (1990)). The rest are rat cDNA clones. The genomic clones have not been reported for any of the PI-PLC enzymes.

All mammalian tissues which have been studied exhibit one or more PI-PLC enzymes. Generally, more than one enzyme exists in a single mammalian cell type. PI-PLC enzymes do exhibit tissue selectivity in their distribution. PLC-$\beta$ is found predominantly in neural tissues and is the major enzyme in the brain. PLC-$\gamma_1$ is found in brain and many peripheral tissues. PLC-$\delta_2$ is found in immune cells, and PLC-$\delta_1$ appears to be predominantly in peripheral tissues. To date, a PI-PLC enzyme found exclusively in inflammatory cells has not been reported.

Point mutations of PLC-$\delta$1 have been identified in the spontaneously hypertensive rat genome (Yagisawa et al., *J. Hypertens.* 9: 997–1004 (1991)). Biochemical studies have demonstrated the activation of PLC-$\delta$1 (5 fold) in spontaneously hypertensive rats (Kato et al., *J. Biol. Chem.* 267:6483–6487 (1992)). The point mutations, situated in the putative catalytic domain, may be a major cause of the hypertension related phenomena of abnormal calcium homeostasis, a direct result of PLC-$\delta$1 activation.

PI-PLC-$\delta$2 appears to be an important enzyme in immunocompetent cells (Emori et al., *J. Biol. Chem.*, 264:21885–21890). The protein is a moderately abundant protein comprising 0.1 to 0.05% of total cytosolic protein. No information is available concerning the genetic regulation of PI-PLC enzymes, mRNA or protein stability.

It has been established that a rapid synthesis of prostaglandins (PG) from arachidonic acid in macrophages usually accompanies inflammatory stimuli. Thus, inhibition of the release of arachidonic acid from macrophages would provide an effective control of PG synthesis and thereby inflammatory conditions. Recently, phospholiphase C has been characterized as an enzyme which is involved in the biosynthetic phosphatidylinositol-arachidonic acid-prostaglandin pathway. This finding is further substantiated by the observation that phospholipase C is inhibited by phenothiazine, a compound known to inhibit the stimulated release of arachidonic acid from macrophages and prostaglandins from platelets.

Activation of T cell antigen receptor (TCR/CD3) elicits a cascade of biochemical processes which are responsible for complex biological responses ranging from immune response to inflammation. The activation of PLC$\gamma$1 can also be achieved through the action of nonreceptor protein tyrosine kinases in response to certain cell surface receptors in leukocytes (TCR) (Park et al., *Proc. Natl. Acad. Sci. U.S.A.* 88:5453–5456 (1991)). PLC$\gamma$1 activation also occurs upon IgM ligation in B lymphocytes, IgE receptor (Fc$\epsilon$RI) ligation in basophilic leukemia cells and IgG receptor (Fc$\gamma$RI and Fc$\gamma$RII) in monocytic cells (Liao et al., *Proc. Natl. Acad. Sci. U.S.A.* 89:3659–3663 (1992)). Thus, inhibition of PLC$\gamma$ activity, may be of therapeutic value in the treatment of inflammatory conditions.

PLC$\gamma$ is the only isozyme that is phosphorylated by activated tyrosine kinase growth factor receptors (Rotin et al., *EMBO J.*, 11:559–567 (1992); Mohammadi et al., *Mol. Cell. Biol.*, 11:5068–5078 (1992); Kim et al., *Cell*, 65:435–441 (1991)). Following growth factor stimulation, cytosolic PLCγ is extensively and rapidly phosphorylated in vivo (50–70% of the PLCγ molecules are modified within 5 minutes). This phosphorylation apparently induces the relocation of PLCγ to the plasma membrane where presumably it is better able to interact with its phospholipid substrates. In vitro studies utilizing enzyme that had previously been immunoprecipitated from cells suggest that the catalytic activity of the phosphorylated form of PLCγ1 is increased compared to that of the unphosphorylated form, although this effect also depends on the assay conditions. These results suggest that PLCγ may be an important component of mitogenic signal transduction. Furthermore, altered PLCγ activity may correlate with some disease states. For example, an increase in the concentration of PLCγ has been documented in cells derived from primary human breast carcinomas which also overexpress the EGF receptor (Arteaga et al., *Proc. Natl. Acad. Sci. U.S.A.*, 88, 10435–10439 (1991)). Thus, inhibition of PLCγ activity, particularly of the activated form, may be of therapeutic value in the treatment of breast cancer.

In addition, PLCγ$_1$ has been localized in vivo (immuno-histochemistry) through many layers of the epidermis from a diverse series of hyperproliferative skin conditions, such as psoriasis, seborrheic keratosies and acrochordons (Nanney et al., *Cell Growth and Differentiation*, 3:233–239 (1992)). Thus inhibition of PLCγ activity may be of therapeutic value in treating benign epidermal hyperplasia.

The recent demonstration that specific members of the Gq subfamily can activate different PLC-β isozymes (e.g. Gqα activates PLC-β1 ) (Smrcka et al., *Science* 25 1:804–807 (1991); Taylor et al., *FEBS* 286:214–216 (1991)) provides a connection of PLC-β to a number of transmembrane signal transduction pathways. NIH3T3 cells transfected with an activated mutant of Gqα display a fully transformed phenotype, are highly tumorigenic in athymic nude mice (Kalinec et al., *Mol. Cell Biol.* 12:4687–4693 (1992)) and display greatly enhanced phospholipase C (PLC-β) activity (DeVivo et al., *J. Biol. Chem.* 267:18263–18266 (1992)). Other mutatations in genes for the α subunits of some heterotrimeric G proteins (Lyons et al., *Science* 249:655–659 (1990); Vallar et al., *Nature* 330:556–558 (1987)), have been described and are associated with certain human endocrine tumours suggesting that activated G proteins may play a role in the oncogenic process. Thus, PLC-β in addition to PLCT may be associated with human cancer.

Accordingly, it is an object of this invention to provide specific and selective inhibitors of phospholipase C which can be potent anti-inflammatory and analgesic agents useful in the treatment of inflammatory conditions, including rheumatoid arthritis, emphysema, bronchial inflammation, osteoarthritis, spondylitis, lupus, psoriasis, acute respiratory distress syndrome, gout, fever, and pain.

It is also the object of this invention to provide inhibitors of phospholipase C which are pharmaceutical agents useful in the treatment of certain forms of cancer, including breast cancer, and other hyperproliferative disease states of the epidermis.

Another object of this invention is to provide pharmaceutical compositions to be used in the administration of the novel phospholipase C inhibitors.

Still a further object of this invention is to provide a method of controlling and treating inflammation and pain by administering an effective amount of the compounds of the instant invention in a mammalian species in need of such treatment.

Figure 1:
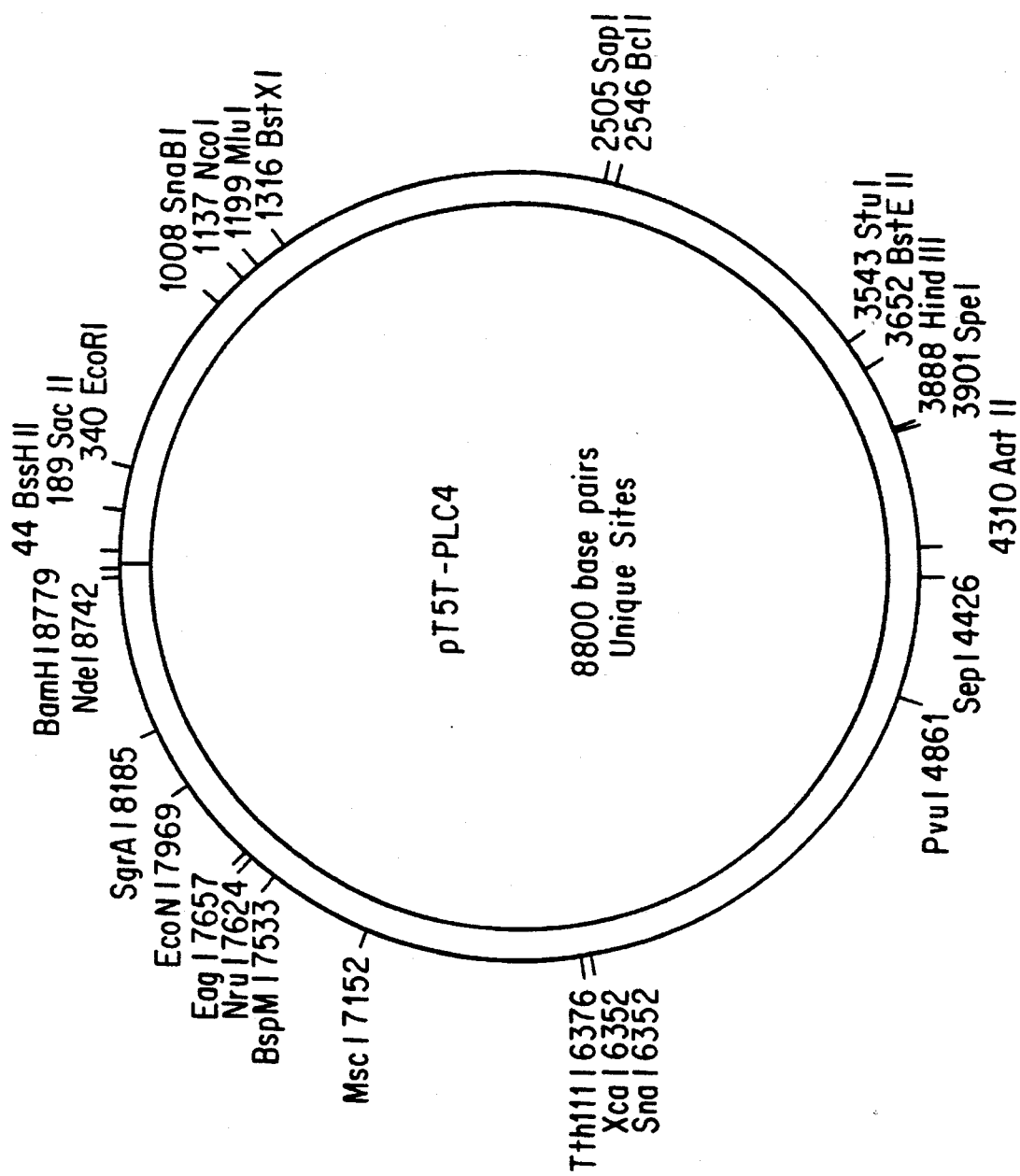
FIG. 1. Plasmid pT5T-PLC4

A schematic depiction of the construction of plasmid pT5T-PLC4 is shown.

FIGS. 2a–2e. PLC γ$_1$ amino acid sequence and cDNA encoding sequence

The nucleotide sequence which encodes PLC γ$_1$ is shown along with the corresponding amino acids of PLC γ$_1$ which are provided underneath the cDNA sequence. The codons at 2833–2838 have been changed from the natural AGGAGG tandem to CGGCGG. (cDNA: SEQ.ID.NO.: 1; amino acid: SEQ.ID.NO.: 2)

FIGS. 3a–3e. cDNA encoding sequence which includes the epitope tag

Nucleotide sequence used for expression and purification of PLC γ$_1$ (1-3879; end indicated by "*") and the neighboring BamlI restriction site. The amino acid sequence of the longest open reading frame (1291 aa) is provided underneath the corresponding nucleotides. (cDNA: SEQ.ID.NO.: 3; amino acid: SEQ.ID.NO.: 2)

DETAILED DESCRIPTION OF THE INVENTION

This invention relates to novel α-hydroxyphosphonate compounds of the structural formula I:

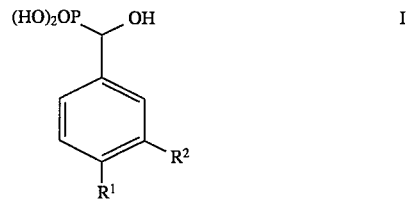

or a pharmaceutically acceptable salt or ester thereof, wherein:

$R^1$ and $R^2$ are independently selected from:
a) hydrogen; and
b)

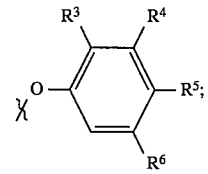

provided that if $R^1$ is hydrogen, $R^2$ is substituent b) and if $R^2$ is hydrogen, $R^1$ is substituent b); and $R^3$, $R^4$, $R^5$ and $R^6$ are independently selected from the group consisting of:
a) hydrogen;
b) halogen;
c) $C_1$–$C_4$-alkyl;
d) $C_1$–$C_4$-alkoxy; and
e) hydroxy, provided that at least one of $R^3$, $R^4$, $R^5$ and R6 is a substituent other than hydrogen; or $R^3$ and $R^4$ or $R^4$ and $R^5$ are combined to form a —$CH_2CH_2CH_2CH_2$— diradical.

An embodiment of the instant invention is a compound having the formula I wherein the substitutents $R^1$ and $R^2$ are as described hereinabove and wherein substituents $R^3$, $R^4$, $R^5$ and $R^6$ are as described hereinabove provided, however, that both $R^3$ and $R^4$ are not methyl if $R^5$ is hydrogen and $R^3$ and $R^4$ or $R^4$ and $R^5$ are not combined to form a —$CH_2CH_2CH_2CH_2$—diradical.

The alkyl substituents recited above denote straight and branched chain hydrocarbons of the length specified such as methyl, ethyl, isopropyl, isobutyl, etc.

The alkoxy substituent represents an alkyl group as described above attached through an oxygen bridge.

The term "halogen" represents substituents selected from iodide, chloride, bromide and fluoride.

Specific compounds of the instant invention include the compounds having the formula

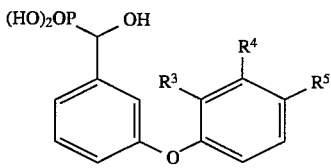

wherein

| $R^3$ | $R^4$ | $R^5$ |
| --- | --- | --- |
| H | H | —$OCH_3$ |
| H | H | —Cl |
| H | —Cl | H |
| —Cl | H | H |
| H | H | —$CH_3$ |
| H | H | —OH |
| H | —Cl | —Cl |

Other compounds of the instant invention include compounds having the formula:

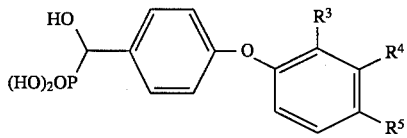

wherein:

| $R^3$ | $R^4$ | $R^5$ |
| --- | --- | --- |
| H | —Cl | H |
| H | —$OCH_3$ | H |
| H | —$CH_2CH_3$ | H |
| —$CH_3$ | —$CH_3$ | H |

Still other compounds of the instant invention include the following compounds:

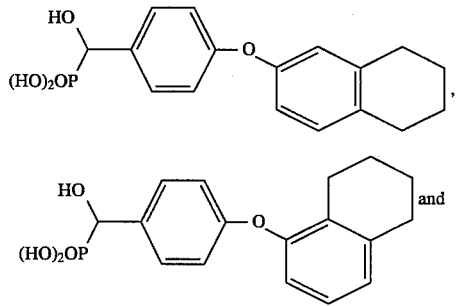

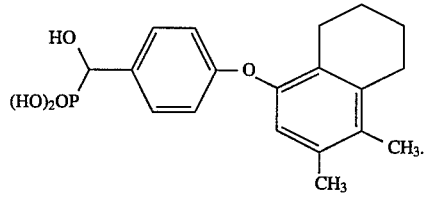

The novel compounds of the present invention are generally prepared by a process (illustrated in Scheme 1) comprising the treatment of an appropriate halogenated benzaldehyde with a suitably substituted phenol to provide the phenoxy benzaldehyde of the Formula II. This benzaldehyde is then reacted with a suitable dialkyl phosphite which provides the compound of Formula I upon saponification of the phosphonate moiety.

SCHEME 1

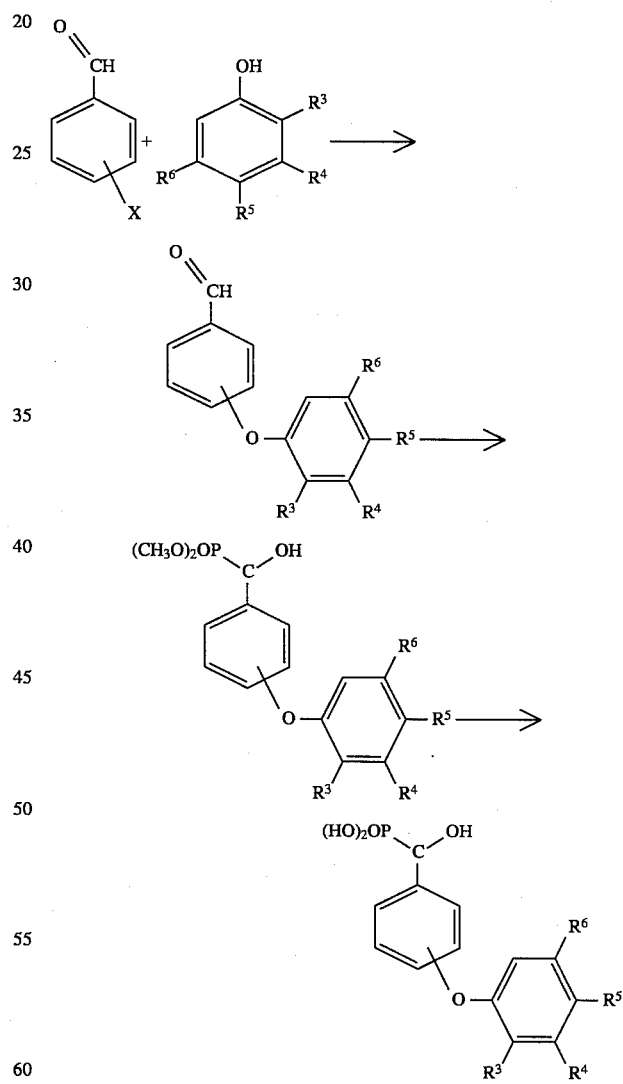

The starting materials of the process described above are commercially available or known in the literature.

The compounds of this invention form salts with various inorganic and organic acids and bases which are also within the scope of the invention. Such salts include ammonium salts, alkali metal salts like sodium and potassium salts, alkaline earth metal salts like the calcium and magnesium salts, salts with organic bases; e.g., dicyclohexylamine salts, N-methyl-D-glucamine, salts with amino acids like arginine, lysine, and the like.

The non-toxic, physiologically, acceptable salts are preferred, although other salts are also useful; e.g., in isolating or purifying the product.

The salts can be formed by conventional means such as by reacting the free acid forms of the product with one or more equivalents of the appropriate base in a solvent or medium in which the salt is insoluble, or in a solvent such as water which is then removed in vacuo or by freeze-drying or by exchanging the cations of an existing salt for another cation on a suitable ion exchange resin.

It will be further appreciated that the compounds of general Formula I in this invention may be derivatized at functional groups to provide prodrug derivatives which are capable of conversion back to the parent compounds in vivo. The concept of prodrug administration has been extensively reviewed (e.g. A. A. Sinkula in *Annual Reports in Medicinal Chemistry*, Vol. 10, R. V. Heinzelman, Ed., Academic Press, New York Lond, 1975, Ch. 31, pp. 306–326), H. Ferres, *Drugs of Today*, Vol. 19, 499–538 (1983) and *J. Med. Chem.*, 18, 172 (1975).

Mode of Administration and Pharmaceutical Compositions.

Because of their ability to inhibit the enzymatic activity of the various forms of phospholipase C, the compounds of Formula I of the present invention can be used to reduce inflammation and relieve pain in diseases such as rheumatoid arthritis, emphysema, bronchial inflammation, osteoarthritis, spondylitis, lupus, psoriasis, acute respiratory distress syndrome, gout, rheumatic fever and the like. Furthermore the compounds can also be used to treat cancer, especially certain forms of cancer associated with phospholipase C, such as primary human breast carcinomas.

When the compounds of formula I are utilized in vivo, such compounds can be administered orally, topically, parentally, by inhalation spray or rectally in dosage unit formulations containing conventional non-toxic pharmaceutically acceptable carriers.

Accordingly, the present invention also provides pharmaceutical compositions comprising the compounds of formula I with a pharmaceutically acceptable carrier.

The term parenteral as used herein includes subcutaneous injections, intravenous, intramuscular, intrasternal injection or infusion techniques. In addition to the treatment of mammals, such as mice, rats, horses, dogs, cats, etc., the compounds of the invention are effective in the treatment of humans.

Pharmaceutical compositions of this invention comprise compounds of Formula I and pharmaceutical carders suitable for the route of administration. Standard methods for formulating pharmaceutical composition of this type may be found in *Remington's Pharmaceutical Sciences*, Mack Publishing Company, Easton, Pa.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparation.

Formulations for oral use include tablets which contain the active ingredient in admixture with non-toxic pharmaceutically acceptable excipients. These excipients may be, for example, inert diluents, such as calcium carbonate, sodium carbonate, lactose, calcium phosphate or sodium phosphate, granulating and disintegrating agents, for example, maize starch, or alginic acid; binding agents, for example, starch, gelatin or acacia, and lubricating agents, for example, magnesium stearate, stearic acid or talc. The tables may be uncoated or they be coated by known techniques to delay disintegration and absorption in the gastrointestinal tract and thereby provide a sustained action over a longer period. For example, a time delay material such as glyceryl monostearate or glyceryl disterate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin, or olive oil.

A typical tablet or capsule may contain the following:

| Ingredient | Percent w/w |
| --- | --- |
| Lactose, spray-dried | 40–99 |
| Magnesium stearate | 1–2 |
| Cornstarch | 10–20 |
| Active ingredient | 0.001–20 |

The pharmaceutical compositions of the invention may also be in the form of oil-in-water emulsions. The oily phase may be a vegetable oil, for example, olive oil or arachis oils, or a mineral oil, for example, liquid paraffin or mixtures of those. Suitable emulsifying agents may be naturally-occurring gums, for example, gum acacia or gum tragacanth, naturally-occurring phosphatides, for example, soybean lecithin; and esters including partial esters derived from fatty acids and hexitol anhydrides, for example, sorbitan monooleate, and condensation products of said partial esters with ethylene oxide, for example, polyoxyethylene sorbitan mono-oleate. The emulsions may also contain sweetening and flavoring agents.

Syrups and elixirs may be formulated with sweetening agents, for example, glycerol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above.

Parenteral compositions are prepared in conventional suspension or solution forms, as emulsions or as solid forms for reconstruction. Suitable carders are water, saline, dextrose, Hank's solution, Ringer's solution, glycerol, and the like. Parenteral administration is usually by injection which may be subcutaneous, intramuscular or intravenous.

The sterile injectable prepartion may be sterile injectable solution or suspension in a non-toxic parenterally-acceptable diluent or solvent. Among the acceptable vehicles and solvents that may be x s employed are water, 1,3-butanediol. Ringer's solution and isotonic sodium chloride solution. In addition, sterile fixed oils are conventionally employed as a solvent or suspending medium. For this purpose any bland fixed oil may be employed including synthetic mono- or diglycerides. Fatty acids such as oleic acid also find use in the preparation of injectables.

The compounds of formula I can also be administered in the form of suppositories for rectal administration of the drug. These compositions can be prepared by mixing the drug with a suitable non-irritating excipient which is solid at ordinary temperatures but liquid at the rectal temperature and while therefore melt in the rectum to release the drug, for example, cocoa butter and polyethylene glycols.

When the compounds of formula I are utilized in vivo, dosage levels on the order of from about 0.2 mg to about 300 mg, preferably from about 10 mg to about 100 mg, per kilogram of body weight per day are useful.

Aqueous suspensions usually contain the active materials in admixture with appropriate excipients. Such excipients are suspending agents, for example, sodium carboxymethylcellulose, methylcellulose, hydroxypropymethylcellulose, sodium alinate, polyvinylpyrolidone, gum tragacanth and gum acacia; dispersing or wetting agents which may be a naturally-occuring phosphatide, for example, lecithin; a condensation product of an alkylene oxide with a fatty oxide, for example, polyoxyethylene stearate; a condensation product of ethylene oxide with a long chain aliphatic alcohol, for example, heptadecaethyleneoxycetanol; a condensation product of ethylene oxide with a partial ester derived from fatty acids and a hexitol such as polyoxyethylene sorbitol monooleate; or a condensation product of ethylene oxide with a partial ester derived from fatty acids and hexitol anhydrides, for example, polyoxyethylene sorbitan monooleate. The aqueous suspensions may also contain one or more preservatives, for example, ethyl, n-propyl, or p-hydroxybenzoate; one or more coloring agents; one or more flavoring agents; and one or more sweetening agents such as sucrose or saccharin.

Oily suspension may be formulated by suspending the active ingredients in a vegetable oil, for example, arachis oil, olive oil, sesame oil or coconut oil, or in a mineral oil such as liquid paraffin. The oily suspension may contain a thickening agent, for example, beeswax, hard paraffin or cetyl alcohol. Sweetening agents such as those set forth above and flavoring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending and one or more preservatives. Suitable dispersing or wetting agents and suspending agents are exemplified by those already mentioned above. Additional excipients, for example, sweetening, flavoring and coloring agents, may also be present.

For topical administration, the pharmaceutical composition may be in the form of a salve, cream, ointment, spray, powder or the like. Standard pharmaceutical carriers for such compositions may be used. Preferably, compositions for topical administration will contain 0.05–5% of the active ingredient.

A typical cream formulation may contain the following:

| Ingredient | Parts by Weight |
| --- | --- |
| Water/glycol mixture (15% or more glycol) | 50–99 |
| Fatty alcohol | 1–20 |
| Non-ionic surfactant | 0–10 |
| Mineral oil | 0–10 |
| Typical pharmaceutical adjuvants | 0–5 |
| Active ingredient | 0.05–5 |

A typical ointment formulation may contain the following:

| Ingredient | Parts by Weight |
| --- | --- |
| White petrolatum | 40–99 |
| Mineral oil | 5–20 |
| Glycol solvent | 1–15 |
| Surfactant | 0–10 |
| Stabilizer | 0–10 |
| Active Ingredient | 0.05–5 |

The compounds of this invention may be combined with other known anti-inflammatory/immunosuppressive agents such as steroids or non-steroidal anti-inflammatory agents (NSAID) in the pharmaceutical compositions and methods described herein.

Dosage levels of the order from 0.1 mg to 140 mg per kilogram of body weight per day are useful in the treatment of the above-indicated conditions (10 mg to 7 gms per patient per day). For example, inflammation is effectively treated and anti-pyretic and analgesic activity manifested by the administration from about 0.5 to 50 mg of the compound per kilogram of body weight per day (25 mg to 3.5 gms per patient per day). Preferably, a dosage of from about 2 mg to about 20 mg per kilogram of body weight per day is used to produce effective results (50 mg to 1 gm per patient per day).

Similarly with regard to treatment of certain forms of cancer, administration is in an amount between about 0.1 mg/kg of body weight to about 20 mg/kg of body weight per day, preferably of between 0.5 mg/kg of body weight to about 10 mg/kg of body weight per day.

The amount of active ingredient that may be combined with the carrier materials to produce a single dosage form will vary depending upon the host treated and the particular mode of administration. For example, a formulation intended for the oral administration of humans may contain from 5 mg to 5 gm of active agent compounded with an appropriate and convenient amount of carrier material which may vary from about 5 to 95 percent of the total composition. Dosage unit forms will generally contain between about 25 mg to about 500 mg of active ingredient.

It will be understood, however, that the specific dose level for any particular patient will normally be determined by the prescribing physician and will depend upon a variety of factors including the activity of the specific compound employed, the age, body weight, general health, sex, diet, time of administration, route of administration, rate of excretion, drug combination and the severity of the particular disease undergoing therapy.

EXPERIMENTAL PROCEDURES

EXAMPLE 1

1-Hydroxy-1-(3-(3-chlorophenoxy)phenyl)-methylphosphonic acid

Step A: 3-(3-Chlorophenoxy)benzaldehyde

A mixture of 3-bromobenzaldehyde (6.0g), 3-Chlorophenol (4.8g), sodium hydride (1.3 g of an 80% suspension in oil) and cuprous cloride (1 g) was heated under reflux in pyridine (125 ml) under an atmosphere of nitrogen gas for 16 hours. The mixture was cooled, diluted with water, acidified with hydrochloric acid and extracted with diethyl ether. The etheral extracts were dried ($Na_2SO_4$), concentrated and purified by chromatography on silica gel eluting with ethyl acetate-petroleum ether (1:9) to give the title compound as a colourless oil.

Step B: Dimethyl 1-Hydroxy-1-(3-(3-chlorophenoxy)phenyl)methylphosphonate

The foregoing aldehyde (1.5 g) was stirred for 24 hours in a mixture of triethylamine (0.9 ml) and dimethyl phosphite (0.89 ml). The mixture was evaporated under reduced pressure and crystallised from ethyl acetate to give the tile compound as a white solid.

Step C: 1-Hydroxy-1-(3-(3-chlorophenoxy)phenyl)methylphosphonic acid

The phosphonate ester of part b) (0.5 g) was treated with trimethylsilyl bromide (0.96 ml) for 16 hours after which time the mixture was evaporated under reduced pressure and the residue dissolved in methanol (5 ml) for 10 minutes. The solution was concentrated and the residue dissolved in water and freeze dried to give the title compound as a white solid, $^1$H NMR (360 MHz, $d_6$ DMSO) δ4.70 (1H, d, J=14 Hz), 6.91–6.97 (2H, m), 7.02 (1H, t, J=2.2 Hz), 7.13 (1H, d, J=1.5 Hz), 7.17 (1H, d, J=6.2 Hz), 7.23 (1H, d, J=7.4 Hz), 7.32–7.40 (2H, m).

Examples 2–7 were prepared by the method of Example 1 using the appropriately substituted phenol.

EXAMPLE 2

1-Hydroxy-1-(3-phenoxyphenyl)methylphosphonic acid $^1$H NMR (360 MHz, $D_2O$) δ4.93 (1H, d, J=12.8 Hz), 7.00 (1H, d, J=8.1 Hz), 7.08 (2H, d, J=7.8 Hz), 7.14 ( 1 H, d, J=1.9 Hz), 7.20 ( 1H, t, J=7.6 Hz), 7.25 (1H, d, J=7.6 Hz), 7.38–7.45 (3H, m).

EXAMPLE 3

1-Hydroxy-1-(3-(3,4-dichlorophenoxy)phenyl)methylphosphonic acid $^1$H NMR (360 MHz, $d_6$ DMSO) δ4.70 (1H, d, J=14.3 Hz), 6.94–7.01 (2H, m), 7.12 (1H, d, J=1.7 Hz), 7.23–7.25 (2H, m), 7.35 (1H, t, J=7.8 Hz), 7.61 (1H, d, J=8.9 Hz).

EXAMPLE 4

1-Hydroxy-1-(3-(4-chlorophenoxy)phenyl)methylphosphonic acid $^1$H NMR (360 MHz, $d_6$ DMSO) δ4.67 (1H, d, J=14.3 Hz), 6.88 (1H, d, J=7.0 Hz), 7.00–7.02 (2H, dd, J=2.1 and 8.9 Hz), 7.09 (1H, s) 7.19 (1H, d, J=7.0 Hz), 7.31 (1H, t, J=7.0 Hz), 7.39–7.42 (2H, dd, J=2.1 and 8.9 Hz).

EXAMPLE 5

1-Hydroxy-1-(3-(2-chlorophenoxy)phenyl)methylphosphonic acid $^1$H NMR (360 MHz, $d_6$ DMSO) δ4.68 (1H, d, J=14.3 Hz), 6.79 (1H, d, J=8.0 Hz), 7.03–7.06 (2H, m), 7.17–7.21 (2H, m), 7.27–7.36 (2H, m), 7.58 (1H, dd, J=8.0 and 1.6 Hz).

EXAMPLE 6

1-Hydroxy-1-(3-(4-methoxyphenoxy)phenyl)methylphosphonic acid $^1$H NMR (360 MHz, $d_6$ DMSO) δ3.74 (3H, s), 4.65 (1H, d, J=14.2 Hz), 6.76 (1H, d, J=7.8 Hz), 6.93–7.02 (5H, m), 7.09 (1H, d, J=7.8 Hz), 7.23 (1H, t, J=7.8 Hz).

EXAMPLE 7

1-Hydroxy-1-(3-(4-methylphenoxy)phenyl)methylphosphonic acid $^1$H NMR (360 MHz, $d_6$ DMSO) δ2.28 (3H, s), 4.65 (1H, d, J=14.2 Hz), 6.80 (1H, d, J=8 Hz), 6.90 (2H, d, J=9 Hz), 7.04 (1H, d, J=1.5 Hz), 7.12 (1H, d, J=8 Hz), 7.17 (2H, d, J=9 Hz), 7.27 (1H, t, J=8 Hz).

EXAMPLE 8

1-Hydroxy-1-(3-(4-hydroxyphenoxy)phenyl)methylphosphonic acid

Dimethyl 1-Hydroxy- 1-(3-(4-methoxyphenoxy)phenyl)methylphosphonate was prepared by the method of Example 1a) and 1b) using 4-methoxyphenol. A solution of this compound (150 mg) in dry dichloromethane (10 ml) at −78° C. under an atmosphere of nitrogen was treated with boron tribromide (4 ml of a 1M solution in dichloromethane). The solution was allowed to warm to 20° C. then concentrated under reduced pressure. The residue was treated with trimethylsilyl bromide (1.2 ml) for 3 hours then concentrated and dissolved in methanol. After 10 minutes the solution was concentrated under reduced pressure. The residue was dissolved in water and freeze dried to give the title compound as a white solid, $^1$H NMR (360 MHz, $D_2O$) δ4.93 (1H, d, J=12.6 Hz), 6.88–7.02 (5H, m), 7.07 (1H, d, J=1.8 Hz), 7.19 (1H, d, J=7.5 Hz), 7.37 (1H, t, J=7.5 Hz).

EXAMPLE 9

1-Hydroxy-1-(4-(3-chlorophenoxy)phenyl)methylphosphonic acid

Step A: 4-(3-Chlorophenoxy)benzaldehyde

3-Chlorophenol (1.9 g) was stirred with 4-fluoro-benzaldehyde (1.8 g) and sodium hydride (0.46 g of an 80% suspension in oil) in dimethylformamide (50 ml) at 110° C. under an atmosphere of nitrogen for 16 hours. The solution was diluted with water and extracted with diethyl ether. The ethereal extract was dried ($Na_2SO_4$), concentrated and purified by chromatography on silica gel eluting with ethyl acetate-petroleum ether (1:9) to give the title compound as a colourless oil.

Step B: 1-Hydroxy-1-(4-(3-chlorophenoxy)phenyl)methylphosphonic acid

This was prepared from 4-(3-Chlorophenoxy)benzaldehyde using the methods of Example 1b) and 1c). $^1$H NMR (360 MHz, $d_6$ DMSO) δ4.69 (1H, d, J=13.6 Hz), 6.92–7.02 (4H, m), 7.15–7.18 (1H, m), 7.37–7.46 (3H, m).

EXAMPLE 10

1-Hydroxy-1-(4-(3-ethylphenoxy)phenyl)methylphosphonic acid

Prepared by the method of Example 9 using 3-ethylphenol. $^1$H NMR (360 MHz, $d_4$ MeOH/CDCl$_3$) δ1.21 (3H, t, J=7.6 Hz), 2.61 (2H, q, J=7.6 Hz), 4.90 (1 H, d, J=11.7 Hz), 6.78 (1H, dd, J=2.1 and 8.0 Hz), 6.84 (1H, s), 6.94 (1H, d, J=7.0 Hz), 6.97 (2H, d, J=8.6 Hz), 7.22 (1H, t, J=7.8 Hz), 7.46 (2H, dd, J=1.8 and 8.6 Hz).

EXAMPLE 11

1-Hydroxy-1-(4-(3-methoxyphenoxy)phenyl)-methylphosphonic acid

Prepared by the method of Example 9 using 3-methoxyphenol and convened to the bis-cyclohexylammonium salt by treating with cyclohexylamine in a mixture of methanol and ethylacetate, then filtering and drying. $^1$H NMR (360 MHz, D$_2$O) δ1.14–1.40 (10H, m), 1.63–1.67 (2H, m), 1.77–1.81 (4H, m), 1.96–1.99 (4H, m), 3.09–3.16 (1H, m), 3.80 (3H, s), 4.71 (1H, d, J=11.4 Hz), 6.71–6.73 (2H, m), 6.78–6.81 (1H, m), 7.06 (2H, d, J=8.6 Hz), 7.32–7.37 (1H, m), 7.48 (2H, d, J=8.6 Hz).

EXAMPLE 12

Assay Protocol for Evaluating Inhibition of Phospholipase Cγ

General. Competent DH5α cells (subcloning efficiency) were obtained from GIBCO/BRL (Gaithersburg, Md.). Competent BL21(DE3) cells were purchased from Novagen (Madison, Wis.). PCR mutagenesis was carried out according to literature protocol (Higuchi, 1990). The general cloning vector, pBSII(S/K)+, was from Stratagene (La Jolla, Calif.). pT5T was constructed as described (Eisenberg et al., 1990). DNA sequencing was performed at each sequence modification on the relevant portion of the gene using the dideoxy chain termination method (Sanger et al., 1977) to verify the change to the wild type cDNA. Standard DNA manipulations were carded out as described (Sambrook et al., 1989).

Oligonucleotides. Synthetic deoxyribonucleotides were obtained from Midland Certified Reagent Co. (Midland, Tex.). The sequences of the oligonucleotides are (5' to 3'):

```
01 CCC—GGG—CAT—ATG—GAT—CCA—TTG—GAG—GAT—GAT—TAA—
   ATG—GCG—GGC—GCC—GCG—TCC (SEQ. ID. NO.: 4)
02 CTG—CTT—CCG—GAG—CCA—CCT—CTC (SEQ. ID. NO.: 5)
03 TC—GCC—ATT—CGT—CCT—GAG—GGC (SEQ. ID. NO.: 6)
04 GG—GCC—CAA—GCT—TCT—AGA—CTA—AAA—TTC—TTC—GAG—
   GCG—GTT—GTC—TCC—ATT—GAC—CCG—AGT—TCG—TCG
   (SEQ. ID. NO.: 7)
05 G—ATG—ATG—GAG—CGG—CGG—AAG—AAG—ATC—G
   (SEQ. ID. NO.: 8)
06 C—GAT—CTT—CTT—CCG—CCG—CTC—CAT—CAT—C
   (SEQ. ID. NO.: 9)
```

Subcloning of the PLCγ Coding Sequence. Rat brain cDNA is synthesized using rat brain poly(A)RNA as template by literature protocol (Sanbrook, J. et al., *Molecular Cloning: A Laboratry Manual*, Cold Spring Harbor Laboratory Press, Cold Spring Harbor, N.Y.). From the published cDNA sequence of rat brain PLCγ$_1$ (Suh, P.-G., Ryu, S. H., Moon, K. H., Suh, H. W., & Rhee, S. G. (1988) *Proc. Natl. Acad. Sci. USA* 85, 5419–5423), PCR primers, one which contains a BamHI restriction site upstream of the sequence complementary to the 5' end of the PLCγ$_1$ gene (primer 01), and the other one which contains a HindIII site downsteam of the 3' end of the PLCγ gene (primer 04), were synthesized. Carrying out the PCR using these primers (01 and 04) with the above mentioned rat brain cDNA as template, a DNA fragment with the entire rat brain PLCγ$_1$ coding sequence, flanked by a 5' BamHI site and a 3' HindIII site, is generated. This BamHI-HindIII fragment containing the coding sequence of PLCγ was subcloned into pBSII(S/K)+, generating pPLC1. The rest of the manipulations were accomplished using PCR to generate the appropriate DNA fragment. The 5' end of the PLC$_{γ1}$ gene was altered to include a new BamHI site and a sequence that would eventually translationally couple the expression of PLCγ$_1$ to the φ10 gene of the pT5T vector as described by Eisenberg, S. P., Evans, R. J., Arend, W. P., Verderber, E., Brewer, M. T., Hannum, C. H., & Thompson, R. C. (1990) *Nature*(London) 343, 341–346.

Primers 01 and 02 were used to generate a 508 bp fragment (from template DNA pPLC1) containing a 5' BamHI site and 3' EcoRI site. This new restriction fragment was substituted for the analogous fragment in pPLC1 to produce pPLC2.

PCR-mediated mutagenesis with template pPLC2 and with primers 03–05 to generate one mutant fragment and primers 04–06 to generate the second mutant fragment was used to restructure the 3' end, to add DNA sequence encoding the epitope tag Glu-Glu-Phe (which is recognized by the monoclonal antibody YL1/2) (Kilmartin, J. V., Wright, B., & Milstein, C. (1982) *J. Cell. Biol.* 93,576–582), and to change the tandem AGG-AGG codons to CGG-CGG at amino acid positions 944–945 and 1279–1280. Tandem AGG codons are associated with poor protein expression in *E. coli* (Bonekamp, F., & Jensen, K. (1988) *Nucl. Acids Res.* 17, 3013–3024).

Using the isolated mutant fragments from each of these PCRs together as template, the final PCR was carried out using primers 03–06 which yielded, after restriction enzyme digestion, a SphI and HindIII fragment which was used to replace the analogous fragment in pPLC2. The resulting plasmid, pPLC3, contained the coding sequence of the PLCγ$_1$ gene on a BamHI-HindIII fragment with both the sequence encoding the Glu-Glu-Phe tag at the 3' end as well as the changed AGG codons. FIG. 3 shows the final cDNA sequence encoding the enzyme and its epitope tag. (SEQ.ID.NO.: 3) Finally, the BamHI-HindIII fragment from pPLC3 was transferred into the BamHI-HindIII site of pT5T, generating pT5T-PLC4. This construct was used to produce PLCγ$_1$ (containing the Glu-Glu-Phe epitope tag at the C-terminus) translationally coupled to the expression of p10 protein in the pT5T vector.

Expression and Purification of PLCγ$_1$. To express PLCγ$_1$ the plasmid pT5T-PLC4 was transformed into *E. coli* BL21 (DE3). The transformed cells were grown in LB media containing ampicillin (100 gg/ml) and tetracycline (12.5 μ/ml) at 20° C. until the optical density of the cultures at 550 nm was equal to 0.8. This transformed bacterial cell has been deposited with the ATCC and has been assigned the number ATCC 69421. Expression of PLCγ$_1$ was then induced by addition of isopropyl β-D-thiogalactopyranoside (0.5 mM final concentration) to the cultures. After growing for another 6 hours the cells were harvested and PLCγ$_1$ was purified as described below. PLCγ was isolated from *E. coli* by resuspending a cell pellet in standard buffer, 50 mM Tris-Cl pH 8.0, 2 mM MgCl$_2$, 10 mM CaCl$_2$, 1 mM EGTA, 5 mM DTT, 5 mM streptomycin sulfate, 1 mM PMSF, 2 μ/ml leupeptin, 2 μ/ml antipain, 10 μ/ml aprotinin (approximately 5 g wet packed cells/10 ml buffer). The resuspended cells were broken by sonication and the cell debris pelleted by centrifugation at 30,000×g at 4° C. for 30 minutes. The soluble fraction was applied at a flow rate of approximately 0.5 ml/min to a 2 ml column of the monoclonal antibody YL1/2(4mg antibody/ml resin) coupled to cyanogen bromide activated Sepharose. The YL1/2 Sepharose column, which binds the epitope tag Glu-Glu-Phe had previously been equilibrated with standard buffer. After loading the protein onto the column, the column was washed with standard buffer (100 mls) PLCγ was eluted with 3×5 ml 5 mM Asp-Phe dipeptide (Sigma) in standard buffer. The column was regenerated by washing with phosphate buffered saline (PBS)+2M NaCl and then stored in PBS+0.02% NaN$_3$ (wt./vol). The PLCγ$_1$ was obtained in >80% purity and in a 0.05 to 0.5% yield based on the total starting soluble $E.$ $coli$ protein. In some cases the the PLCγ$_1$ was futher purified. This is not necessary for routine drug screening. To further purify the PLCγ$_1$ the protein eluted from the YL1/2 column was chromatographed by HPLC on a MonoQ HR 10-10 column (Pharmacia) where buffer A was standard buffer and buffer B was standard buffer+1M KCl. The column was run at 1 ml/min and the gradient was 0–30% B in 40 min., 30–50% B in 50 min., 50–100% "B" in 70 min. PLCγ$_1$ eluted at approximately 25–30% B.

Assay of purified PLCγ$_1$ activitiy. Activity of the purified PLCγ$_1$ was assayed at 30° C. Reactions were never allowed to proceed to more than 10% completion based on the limiting substrate. A typical reaction contained the following: 50 mM HEPES pH7.5, 0.1% Deoxycholate, 3 mM CaCl$_2$, 1 mM EGTA, 0.1 mM DTT with phosphatidyl inositol (1–1000 μM) (PI) and 0.02 uCi [$^3$H]-phosphatidyl inositol (PI) as substrate. The phospholipid components were dried under a gentle stream of nitrogen and resuspended in assay buffer. The substrate mix is then vortexed and sonicated (10 sec. with probe sonicator) to disperse the lipid and form micelles. After thermally preequilibrating the assay mixture in the absence of enzyme, the reaction was initiated by adding PLCγ$_1$. Reactions containing 0.2 ml aliquots were terminated by addition of ¼ volume 1N HCl, 5 mM EGTA and transferred to an ice bath. The quenched reactions are then filtered through a Q sepharose (Pharmacia) column. To prepare the Q sepharose column 1 ml of Q Sepharose slurry is added to a disposable plastic column. The resin is equilibrated by passing through 20 ml of 10 mM NH$_4$H$_2$PO$_4$, pH 3.5. The quenched reaction, typically 200 μl, is applied to the column and 3 ml of 10 mM NH$_4$H$_2$PO$_4$, pH 3.5 is added, the flow through from this step is collected in a scintillation vial, mixed with 10 ml of scintillation fluid and counted in a Beckman LS3801 scintillation counter.

Assay of inhibitory activity of the compounds of the invention. The inhibitory activity of the compounds of formula I against PLCγ$_1$ was assessed by including known concentrations of the compound of formula I in the assay mixture described above prior to the addition of the enzyme. The relative inhibitory concentrations calculated from the assay are shown in Tables 1 and 2.

TABLE 1

| Example No. | R$^3$ | R$^4$ | R$^5$ | IC$_{50}$ (μM) |
|---|---|---|---|---|
| 1 | H | —Cl | H | 10 |
| 2 | H | H | H | 190 |
| 3 | H | —Cl | —Cl | 56 |
| 4 | H | H | —Cl | 36 |
| 5 | —Cl | H | H | 17 |
| 6 | H | H | —OCH$_3$ | 7 |
| 7 | H | H | —CH$_3$ | 13 |
| 8 | H | H | —OH | 3 |

TABLE 2

| Example No. | R$^3$ | R$^4$ | R$^5$ | IC$_{50}$ (μM) |
|---|---|---|---|---|
| 9 | H | —Cl | H | 5 |
| 10 | H | —CH$_2$CH$_3$ | H | 37 |
| 11 | H | —OCH$_3$ | H | 8 |
|  | H | H | H | >300 |

EXAMPLE 13

Assay Protocol for Evaluating Inhibition of Phospholipase C-β and δ

Purification of Phospholipase C-β and δ from Bovine Brain

PLC-β are obtained as described by S. G. Rhee et al., Meth. Enzym., 197:502–511 (1991). Specifically PLC-δ is purified from the cytosolic fraction of bovine brains, while PLC-β is mainly obtained from the particulate fraction. However, since the particulate and cytosolic forms of PLC-β are identical with respect to amino acid sequence, PLC-β-containing fractions pooled during the purification of the cytosolic PLC-δ are combined with the PLC-β fraction from the particulate fraction. A total of 36 bovine brains are used for the purification. Twelve brains are processed at one time.

Step 1: Separation of Cytosolic and Particulate Fractions. Twelve bovine brains are freshly obtained from a local slaughterhouse, and the cerebra (3.3 kg) are homogenized in a Waring blender with 6.6 liters of buffer containing 20 mM Tris-HCl, pH 7.4, 5 mM EGTA, 2 mM phenylmethysulfonyl fluoride (PMSF), and 0.1 mM DTT. The homogenate is centrifuged for 30 min at 13,000 g at 4°. Both the precipitate and supernatant are saved for Steps 2 and 3, respectively.

Step 2: Preparation of Extracts from Particulate Fractions.

The precipitate from Step 1 is resuspended in the same homogenization buffer (6.6 liters) and homogenized again to ensure complete breakage of cells. The homogenate is centrifuged for 30 min. at 13,000 g. The washed pellet is suspended in 2M KCl in homogenization buffer and stirred for 2 hr at 4°. The suspension is then centrifuged for 90 min at 13,000 g. The supernatant is brought to 60% $(NH_4)_2SO_4$ saturation by adding solid salt. This suspension is centrifuged for 30 min at 13,000 g, and the pellet is suspended in 500 ml of homogenization buffer; the suspension is dialyzed overnight against the homogenization buffer. Dialyzed solution is centrifuged for 30 min at 13,000 g to remove insoluble particles, and the supernatant, which is still very turbid, is kept at −20° to be combined with the dialyzed solutions from the two other identical preparations.

Step 3: Preparation of Cytosolic Extracts. The supernatant from Step 1 is adjusted to pH 4.8 with 1M acetic acid. After 30 min at 4°, precipitates are collected by centrifugation and dissolved in 1 liter of homogenization buffer. Insoluble materials are pelleted by centrifuging for 30 min at 13,000 g, and the turbid supernatant is removed for Step 4.

Step 4: Ion-Exchange Chromatography on DEAE-Cellulose.

The supernatant from Step 3 is applied to a DE-52 DEAE-cellulose (Whatman Biosystems, Maidstone, UK) column (8×40 cm), which has been equilibrated with 20 mM Tris-HCl, pH 7.6, 1 mM EGTA, 0.1 mM DTT. The column is eluted with a 6-liter linear KCl gradient from 0 to 225 mM KCl in 50 mM Tris-HCl, pH 7.6, 1 mM EGTA, and 0.1 mM DTT. Three PLC activity peaks are eluted and the peak fractions are pooled separately. The first peak, which contains PLC-δ, is further purified immediately in the next step. The second peak fractions containing PLC-β are concentrated to about 100 ml and combined with the extracts of particulate fractions from Step 2. The third peak fractions containing PLC-γ are discarded.

Purification of PLC-δ

Step 5: Heparin-Agarose Chromatography of PLC-δ. The PLC-β fractions pooled from the previous step (750 ml) are directly applied to a heparin-agarose column (5×15 cm) equilibrated with 20 mM HEPES, pH 7.0, 0.1 mM DTT, and 1 mM EGTA. The column is eluted with a 1.8-liter linear gradient of NaCl from 100 to 700 mM NaCl in equilibration buffer. The peak fractions (240 ml) are pooled, concentrated to approximately 10 ml in an Amicon (Danvers, Mass.) filtration apparatus, and stored frozen to be combined with concentrated fractions of PLC-δ from two other identical preparations.

Step 6: Reversed-Phase Chromatography of PLC-δ, on TSK Phenyl-5-PW. Solid KCl is added to the combined concentrated fractions (35 ml) from Step 5 to give a final concentration of 3M, and the mixtures are centrifuged to remove denatured proteins. The supernatants are applied at a flow rate of 5.0 ml/min to a high-performance liquid chromatography (HPLC) preparative TSK phenyl-5-PW column (21.5×150 mm; Bio-Rad, Richmond, Calif.) equilibrated with 20 mM HEPES, pH 7.0, 3M KCl, 1 mM EGTA, and 0.1 mM DTT. Elution is continued at 5.0 ml/min with a decreasing KCl gradient from 3 to 1.2M KCl for 10 min and with a decreasing KCl gradient from 1.2 to 0M KCl for 20 min. Fractions (25 ml) containing PLC activity are pooled and washed in an Amicon filtration apparatus with 20 mM MOPS buffer, pH 5.7, 0.1 mM DTT, 1 mM EGTA, and finally concentrated to about 10 ml.

Step 7: Ion-Exchange Chromatography of PLC-δ on a Mono S Column. The washed protein solution (~10 ml) from Step 6 is applied at a flow rate of 1.0 ml/min to a Mono S column (70×6 mm, Pharmacia, Piscataway, N.J.) equilibrated with 20 mM MOPS, pH 5.7, 0.1 mM DTT, and 1 mM EGTA. Elution is continued at 1.0 ml/min with a NaCl gradient from 0 to 300 mM NaCl for 20 min and from 300 mM to 1M for 10 min. Peak fractions (1.2 ml) are collected manually, diluted with 2 ml of 20 mM HEPES (ph 7.0), concentrated in a Centricon microconcentrator (Amicon) to approximately 0.5 ml, separated into aliquots, and stored at −20°. A total of 0.3–0.6 mg of homogeneous PLC-δ is obtained, with a yield of 2–4%.

Purification of PLC-β

Step 8: Ion-Exchange Chromatography of PLC-β on DEAE-Cellulose. Because of turbidity, the combined protein solution from Steps 2 and 3 cannot be chromatographed on a DEAE-cellulose column directly. Therefore, two stages of DEAE-cellulose chromatography, a batch procedure followed by a column step, are employed. In the batch step, all of the combined proteins are absorbed on 2 liters of DEAE-cellulose equilibrated with 20 mM Tris-HCl, pH 7.6, containing 5 mM EGTA and 0.1 mM DTT. The DEAE-cellulose slurry is stirred and then collected in a 4-liter sintered glass (coarse) filter funnel. The DEAE-cellulose is washed with the equilibration buffer until it is free of turbid lipid materials and unbound protein. For the column procedure, the washed DEAE-cellulose is removed from the filter funnel, mixed with the equilibration buffer, and poured onto a column already containing a 10 cm high bed of equilibrated DEAE-cellulose (final dimension, 8×45 cm). The column is eluted at a flow rate of 8 ml/min with an 8-liter linear gradient from 0 to 300 mM KCl buffer containing 50 mM Tris-HCl, pH 7.6, 1 mM EGTA, and 0.1 mM DTT. The activity peak is eluted at a KCl concentration of 110 mM. The peak fractions (600 ml) are pooled.

Step 9: Heparin-Agarose Chromatography of PLC-β. The pooled fraction from Step 8 (600 ml) is applied to a heparin-agarose column (5×25 cm) equilibrated with 20 mM HEPES, pH 7.0, 100 mM NaCl, 0.1 mM DTT, and 1 mM EGTA. The column is eluted with a linear gradient from 100 to 500 mM NaCl in 1.5 liters of equilibrium buffer. Peak fractions (310 ml) are pooled and concentrated on an Amicon filter to 27 ml.

Step 10: Reversed-Phase Chromatography of PLC-β on TSK Phenyl-5-PW. Solid KCl is added to the concentrated fractions from Step 9 to give a concentration of 3M, and the mixtures are centrifuged to remove denatured proteins. The supernatants are applied at a flow rate of 5 ml/min to an HPLC preparative phenyl-5-PW column (150×215 mm) equilibrated with 20 mM HEPES, pH 7.0, 3M KCl, 1 mM EGTA, and 0.1 mM DTT. Elution is continued at 5 ml/min with a decreasing KCl gradient from 3 to 1.2M for 15 min and with a decreasing gradient from 1.2 to 0M for 20 min. Then the column is washed with a KCl-free buffer. Fractions containing each of the two peaks of PLC activity (15 ml for fraction M1 and 13 ml for fraction M2) are collected separately. The pooled solutions are washed with a KCl-free 20 mM HEPES, pH 7.0, and are concentrated to 5 ml in an Amicon filter concentrating procedure. Analysis on SDS-polyacrylamide gels indicates that fractions M1 and M2 contain 150-kDa (PLC-β1) and 140-kDa (PLC-β2) forms of PLC, respectively. The two forms are immunologically indistinguishable. Whether PLC-β2 is a proteolytic fragment of PLC-β1 or a product of alternately spliced mRNA is not known. About 15 mg of PLC-β1 and 8 mg of PLC-β2 are obtained.

Assay of inhibitory activity of the compounds of the invention. The inhibitory activity of the compounds of formula I against PLCβ was assessed by including known concentrations of the compound of formula I in an assay mixture similar to the assay mixture described in Example 12, but substituting PLCβ obtained as described above for PLCγ of Example 12, prior to the addition of the enzyme. The relative inhibitory concentrations calculated from the assay are shown in Tables 3 and 4.

TABLE 3

Structure: (HO)₂OP-CH(OH)-phenyl-O-phenyl(R³,R⁴,R⁵)

| Example No. | R³ | R⁴ | R⁵ | IC₅₀ (µM) |
| --- | --- | --- | --- | --- |
| 1 | H | —Cl | H | 24 |
| 2 | H | H | H | >300 |
| 3 | H | —Cl | —Cl | 110 |
| 4 | H | H | —Cl | 65 |
| 5 | —Cl | H | H | 38 |
| 6 | H | H | —OCH₃ | 717 |
| 7 | H | H | —CH₃ | 31 |
| 8 | H | H | —OH | 7 |

TABLE 4

Structure: HO-CH((HO)₂OP)-phenyl-O-phenyl(R³,R⁴,R⁵)

| Example No. | R³ | R⁴ | R⁵ | IC₅₀ (µM) |
| --- | --- | --- | --- | --- |
| 9 | H | —Cl | H | 9 |
| 10 | H | —CH₂CH₃ | H | 74 |
| 11 | H | —OCH₃ | H | 11 |
|  | H | H | H | >300 |

The inhibitory activity of the compounds of formula I against PLCδ is assessed by including known concentrations of the compound of formula I in an assay mixture similar to the assay mixture described in Example 12, but substituting PLCδ obtained as described above for PLCγ of Example 12, prior to the addition of the enzyme.

What is claimed is:

1. A compound of structural formula I:

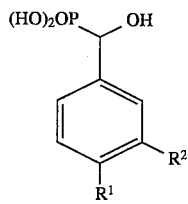

I or a pharmaceutically acceptable salt or ester thereof, wherein:

$R^1$ is: hydrogen;

$R^2$ is:

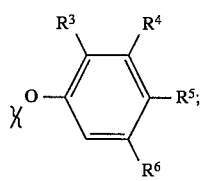

and $R^3$, $R^4$, $R^5$ and $R^6$ are independently selected from the group consisting of:
   a) hydrogen;
   b) halogen;
   c) $C_1$–$C_4$-alkyl;
   d) $C_1$–$C_4$-alkoxy; and
   e) hydroxy, provided that at least one of $R^3$, $R^4$, $R^5$ and $R^6$ is a substituent other than hydrogen and where at least $R^3$ or $R^4$ is hydrogen.

2. The compound according to claim 1 which has the formula:

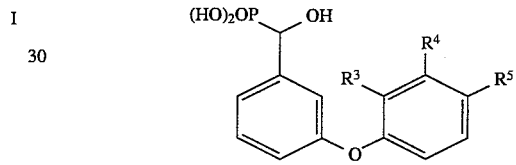

wherein:

| $R^3$ | $R^4$ | $R^5$ |
|-------|-------|-------|
| H  | H   | —OCH$_3$ |
| H  | H   | —Cl |
| H  | —Cl | H |
| —Cl | H  | H |
| H  | H   | —CH$_3$ |
| H  | H   | —OH or |
| H  | —Cl | —Cl. |

3. The compound which has the formula:

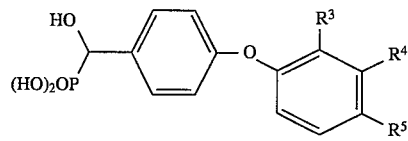

wherein:

| $R^3$ | $R^4$ | $R^5$ |
|-------|-------|-------|
| H | —Cl | H |
| H | —OCH$_3$ | H or |
| H | —CH$_2$CH$_3$ | H. |

4. A compound of structural formula I:

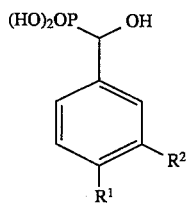

or a pharmaceutically acceptable salt or ester thereof, wherein:

$R^1$ is:

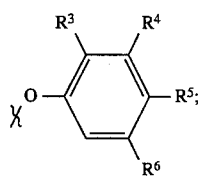

$R^2$ is: hydrogen;

and $R^3$, $R^4$, $R^5$ and $R^6$ are independently selected from the group consisting of:
 a) hydrogen;
 b) halogen;
 c) $C_1$–$C_4$-alkyl;
 d) $C_1$–$C_4$-alkoxy; and
 e) hydroxy, provided that only one of $R^3$, $R^4$, $R^5$ and $R^6$ is a substituent other than hydrogen.

5. A pharmaceutical composition for inhibiting phospholipase C comprising a therapeutically effective amount of a compound of claim 1 and a pharmaceutically acceptable carrier.

6. A pharmaceutical composition for inhibiting phospholipase C comprising a therapeutically effective amount of a compound of claim 4 and a pharmaceutically acceptable carrier.

* * * * *

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 3870 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

```
ATGGCGGGCG CCGCGTCCCC CTGCGCCAAC GGCTGCGGGC CAGCGCGCC  CTCCGAAGCG      60
GAGGTGCTGC ACCTCTGCCG CAGCCTCGAG GTGGGCACCG TCATGACTTT  GTTCTACTCC     120
AAGAAGTCGC AGCGGCCAGA ACGGAAGACC TTCCAGGTCA AGTTGGAGAC  GCGCCAGATC     180
ACATGGAGCC GCGGTGCGGA CAAAATCGAG GGGTCCATCG ATATCCGAGA  AATCAAGGAG     240
ATCCGCCCAG GGAAGACTTC CCGGGACTTT GACCGCTACC AAGAAGACCC  TGCCTTCCGG     300
CCAGATCAGT CACACTGTTT TGTCATCCTC TATGGAATGG AATTCCGCCT  GAAGACCCTG     360
AGCCTGCAAG CCACATCTGA GGATGAAGTG AACATGTGGA TCAAGGGCTT  AACTTGGCTC     420
ATGGAAGATA CGCTGCAGGC GGCCACACCC CTGCAAATTG AGAGATGGCT  CCGGAAGCAG     480
TTCTACTCAG TGGATCGTAA CCGAGAGGAT CGTATATCAG CCAAGGACCT  GAAGAACATG     540
CTGTCACAGG TCAACTACCG GGTCCCCAAC ATGCGCTTCC TCCGAGAGCG  GCTGACGGAC     600
TTTGAACAGC GCAGCGGGGA CATCACCTAT GGGCAGTTTG CTCAGCTTTA  CCGCAGCCTC     660
ATGTACAGCG CCCAGAAGAC GATGGACCTT CCGTTCTTGG AAACCAACAC  TTTGAGGACT     720
GGAGAGCGGC CAGAGCTTTG CCAGGTGTCC CTTTCTGAGT TCCAGCAGTT  CCTTCTTGAG     780
TACCAGGGGG AGCTGTGGGC TGTCGACCGG CTTCAGGTGC AGGAATTTAT  GCTCAGCTTC     840
CTTCGAGACC CCTTGCGAGA GATTGAGGAG CCATACTTCT TCTTGGATGA  GCTTGTCACC     900
TTTCTGTTCT CCAAAGAGAA CAGTGTGTGG AACTCACAGC TGGATGCCGT  GTGCCCAGAA     960
ACCATGAACA ACCCACTGTC TCACTATTGG ATCTCTTCCT CGCATAATAC  GTATCTGACT    1020
```

| | | | | | |
|---|---|---|---|---|---|
| GGGGACCAGT | TCTCCAGCGA | GTCCTCCCTG | GAAGCCTACG | CTCGCTGCCT | GAGGATGGGC | 1080
| TGTCGCTGCA | TCGAGTTGGA | CTGCTGGGAT | GGGCCAGATG | GGATGCCAGT | CATTTACCAT | 1140
| GGGCACACCC | TCACCACCAA | GATTAAGTTC | TCAGATGTCC | TGCACACCAT | CAAGGAGCAC | 1200
| GCGTTCGTAG | CCTCAGAGTA | CCCTGTCATC | CTGTCCATCG | AGGACCACTG | CAGCATTGCC | 1260
| CAGCAGAGGA | ACATGGCCCA | GCACTTCAGG | AAGGTGCTCG | GTGACACGCT | CCTCACCAAG | 1320
| CCCGTGGACA | TTGCCGCTGA | TGGGCTCCCT | TCTCCCAACC | AGCTCAAGAG | GAAGATCCTG | 1380
| ATTAAGCATA | GAAGCTGGC | TGAGGGCAGT | GCCTATGAGG | AGGTGCCTAC | CTCTGTGATG | 1440
| TACTCTGAGA | ATGACATCAG | TAACTCCATC | AAGAATGGTA | TCCTCTACTT | GGAGGACCCC | 1500
| GTGAATCATG | AGTGGTACCC | CCACTACTTT | GTTCTGACTA | GCAGCAAGAT | CTACTACTCT | 1560
| GAGGAGACCA | GCAGTGACCA | GGGAAATGAG | GATGAAGAGG | AGCCGAAGGA | GGCCAGTGGC | 1620
| AGCACAGAGC | TGCACTCGAG | CGAGAAGTGG | TTCCACGGGA | AGCTCGGGGC | TGGGCGCGAC | 1680
| GGGCGGCACA | TTGCTGAGCG | CCTGCTCACC | GAGTACTGCA | TAGAGACTGG | GGCTCCCGAT | 1740
| GGCTCCTTCC | TAGTGCGAGA | AAGTGAGACC | TTCGTGGGGG | ACTACACGCT | GTCTTTTGG | 1800
| CGGAATGGGA | AAGTCCAGCA | CTGCCGTATC | CACTCCCGGC | AGGATGCTGG | GACTCCTAAG | 1860
| TTCTTCTTGA | CAGATAACCT | TGTCTTTGAC | TCTCTCTATG | ACCTCATCAC | ACATTATCAG | 1920
| CAAGTGCCCC | TGCGCTGCAA | TGAGTTTGAG | ATGCGCCTTT | CAGAGCCTGT | TCCACAGACG | 1980
| AATGCCCATG | AGAGCAAAGA | GTGGTACCAC | GCAAGCCTGA | CTAGAGCTCA | GGCTGAACAC | 2040
| ATGCTGATGC | GAGTACCCCG | TGATGGGGCC | TTCCTGGTGC | GGAAGCGCAA | CGAGCCCAAC | 2100
| TCCTATGCCA | TCTCTTTCCG | GGCTGAGGGA | AAGATCAAGC | ACTGCCGAGT | ACAGCAGGAA | 2160
| GGCCAGACTG | TGATGCTGGG | GAACTCTGAG | TTTGACAGCC | TGGTCGACCT | CATCAGCTAC | 2220
| TATGAGAAGC | ATCCCCTGTA | CCGCAAAATG | AAACTGCGCT | ACCCCATCAA | CGAGGAGGCG | 2280
| CTGGAGAAGA | TTGGGACAGC | TGAACCCGAT | TATGGGGCAC | TGTATGAGGG | CCGCAACCCT | 2340
| GGTTTCTATG | TGGAGGCCAA | CCCTATGCCA | ACTTTCAAGT | GTGCAGTAAA | AGCTCTCTTC | 2400
| GACTACAAGG | CCCAGAGAGA | GGATGAGCTG | ACTTTTACCA | AGAGCGCCAT | CATCCAGAAT | 2460
| GTGGAAAAGC | AAGATGGTGG | CTGGTGGCGT | GGGGACTATG | GTGGGAAGAA | GCAGCTGTGG | 2520
| TTCCCCTCAA | ACTATGTGGA | AGAGATGATC | AATCCAGCAA | TCCTAGAGCC | GGAGAGGGAG | 2580
| CATCTGGATG | AGAACAGCCC | ACTGGGGGAC | TTGCTGCGAG | GGTCTTAGA | TGTGCCAGCC | 2640
| TGCCAGATCG | CCATTCGTCC | TGAGGGCAAA | AACAACCGGC | TCTTCGTCTT | CTCCATCAGC | 2700
| ATGCCGTCAG | TGGCTCAGTG | GTCCCTAGAC | GTTGCCGCTG | ACTCACAGGA | GGAGTTGCAG | 2760
| GACTGGGTGA | AAAAGATCCG | TGAAGTTGCC | CAGACTGCAG | ATGCCAGGCT | TACTGAGGGG | 2820
| AAGATGATGG | AGCGGCGGAA | GAAGATCGCC | TTGGAGCTCT | CCGAGCTCGT | GGTCTACTGC | 2880
| CGGCCTGTTC | CCTTTGACGA | AGAGAAGATT | GGCACAGAAC | GCGCTTGTTA | CCGGGACATG | 2940
| TCCTCCTTTC | CGGAAACCAA | GGCTGAGAAG | TATGTGAACA | AGGCCAAAGG | CAAGAAGTTC | 3000
| CTCCAGTACA | ACCGGCTGCA | GCTCTCTCGC | ATCTACCCTA | AGGGTCAGAG | GCTGGACTCC | 3060
| TCCAATTATG | ACCCTCTGCC | CATGTGGATC | TGTGGCAGCC | AGCTTGTAGC | TCTCAATTTT | 3120
| CAGACCCCAG | ACAAGCCTAT | GCAGATGAAC | CAGGCCCTCT | TCATGGCTGG | TGGACACTGT | 3180
| GGCTATGTGC | TGCAGCCAAG | CACCATGAGA | GATGAAGCCT | TTGACCCCTT | TGATAAGAGC | 3240
| AGTCTCCGAG | GTCTGGAGCC | CTGTGTCATT | TGCATTGAGG | TGCTGGGGGC | CAGGCATCTG | 3300
| CCGAAGAATG | GCCGGGGTAT | TGTGTGTCCT | TTCGTGGAGA | TTGAAGTGGC | TGGGGCAGAG | 3360
| TACGACAGCA | CCAAGCAGAA | GACAGAGTTT | GTAGTGGACA | ATGGACTGAA | CCCTGTGTGG | 3420

-continued

```
CCTGCAAAGC CCTTCCACTT CCAGATCAGT AACCCAGAGT TTGCCTTTCT GCGCTTTGTG      3480

GTGTATGAGG AAGACATGTT TAGTGACCAG AACTTCTTGG CTCAGGCTAC TTTCCCAGTA      3540

AAAGGCCTGA AGACAGGATA CAGAGCAGTG CCTTTGAAGA ACAACTACAG TGAAGACCTG      3600

GAGTTGGCCT CCCTGCTCAT CAAGATTGAC ATTTTCCCTG CTAAGGAGAA TGGTGACCTC      3660

AGCCCTTTCA GTGGTACATC CCTAAGGGAA CGGGCCTCAG ATGCCTCCAG CCAGCTGTTC      3720

CATGTCCGGG CCCGGGAAGG GTCCTTTGAA GCCAGATACC AGCAGCCATT TGAAGACTTC      3780

CGCATCTCGC AGGAGCATCT CGCAGACCAT TTTGACAGTC GGGAACGAAG GGCCCCAAGA      3840

AGGACTCGGG TCAATGGAGA CAACCGCCTC                                       3870
```

( 2 ) INFORMATION FOR SEQ ID NO:2:

( i ) SEQUENCE CHARACTERISTICS:
    ( A ) LENGTH: 1290 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:2:

```
Met Ala Gly Ala Ala Ser Pro Cys Ala Asn Gly Cys Gly Pro Ser Ala
 1               5                  10                  15

Pro Ser Glu Ala Glu Val Leu His Leu Cys Arg Ser Leu Glu Val Gly
                20                  25                  30

Thr Val Met Thr Leu Phe Tyr Ser Lys Lys Ser Gln Arg Pro Glu Arg
            35                  40                  45

Lys Thr Phe Gln Val Lys Leu Glu Thr Arg Gln Ile Thr Trp Ser Arg
        50                  55                  60

Gly Ala Asp Lys Ile Glu Gly Ser Ile Asp Ile Arg Glu Ile Lys Glu
65                  70                  75                  80

Ile Arg Pro Gly Lys Thr Ser Arg Asp Phe Asp Arg Tyr Gln Glu Asp
                85                  90                  95

Pro Ala Phe Arg Pro Asp Gln Ser His Cys Phe Val Ile Leu Tyr Gly
               100                 105                 110

Met Glu Phe Arg Leu Lys Thr Leu Ser Leu Gln Ala Thr Ser Glu Asp
           115                 120                 125

Glu Val Asn Met Trp Ile Lys Gly Leu Thr Trp Leu Met Glu Asp Thr
       130                 135                 140

Leu Gln Ala Ala Thr Pro Leu Gln Ile Glu Arg Trp Leu Arg Lys Gln
145                 150                 155                 160

Phe Tyr Ser Val Asp Arg Asn Arg Glu Asp Arg Ile Ser Ala Lys Asp
                165                 170                 175

Leu Lys Asn Met Leu Ser Gln Val Asn Tyr Arg Val Pro Asn Met Arg
            180                 185                 190

Phe Leu Arg Glu Arg Leu Thr Asp Phe Glu Gln Arg Ser Gly Asp Ile
        195                 200                 205

Thr Tyr Gly Gln Phe Ala Gln Leu Tyr Arg Ser Leu Met Tyr Ser Ala
    210                 215                 220

Gln Lys Thr Met Asp Leu Pro Phe Leu Glu Thr Asn Thr Leu Arg Thr
225                 230                 235                 240

Gly Glu Arg Pro Glu Leu Cys Gln Val Ser Leu Ser Glu Phe Gln Gln
                245                 250                 255

Phe Leu Leu Glu Tyr Gln Gly Glu Leu Trp Ala Val Asp Arg Leu Gln
            260                 265                 270
```

```
Val Gln Glu Phe Met Leu Ser Phe Leu Arg Asp Pro Leu Arg Glu Ile
    275                 280                 285

Glu Glu Pro Tyr Phe Phe Leu Asp Glu Leu Val Thr Phe Leu Phe Ser
    290                 295                 300

Lys Glu Asn Ser Val Trp Asn Ser Gln Leu Asp Ala Val Cys Pro Glu
305                 310                 315                 320

Thr Met Asn Asn Pro Leu Ser His Tyr Trp Ile Ser Ser Ser His Asn
                325                 330                 335

Thr Tyr Leu Thr Gly Asp Gln Phe Ser Ser Glu Ser Ser Leu Glu Ala
            340                 345                 350

Tyr Ala Arg Cys Leu Arg Met Gly Cys Arg Cys Ile Glu Leu Asp Cys
        355                 360                 365

Trp Asp Gly Pro Asp Gly Met Pro Val Ile Tyr His Gly His Thr Leu
370                 375                 380

Thr Thr Lys Ile Lys Phe Ser Asp Val Leu His Thr Ile Lys Glu His
385                 390                 395                 400

Ala Phe Val Ala Ser Glu Tyr Pro Val Ile Leu Ser Ile Glu Asp His
                405                 410                 415

Cys Ser Ile Ala Gln Gln Arg Asn Met Ala Gln His Phe Arg Lys Val
            420                 425                 430

Leu Gly Asp Thr Leu Leu Thr Lys Pro Val Asp Ile Ala Ala Asp Gly
        435                 440                 445

Leu Pro Ser Pro Asn Gln Leu Lys Arg Lys Ile Leu Ile Lys His Lys
    450                 455                 460

Lys Leu Ala Glu Gly Ser Ala Tyr Glu Glu Val Pro Thr Ser Val Met
465                 470                 475                 480

Tyr Ser Glu Asn Asp Ile Ser Asn Ser Ile Lys Asn Gly Ile Leu Tyr
                485                 490                 495

Leu Glu Asp Pro Val Asn His Glu Trp Tyr Pro His Tyr Phe Val Leu
            500                 505                 510

Thr Ser Ser Lys Ile Tyr Tyr Ser Glu Glu Thr Ser Ser Asp Gln Gly
        515                 520                 525

Asn Glu Asp Glu Glu Glu Pro Lys Glu Ala Ser Gly Ser Thr Glu Leu
    530                 535                 540

His Ser Ser Glu Lys Trp Phe His Gly Lys Leu Gly Ala Gly Arg Asp
545                 550                 555                 560

Gly Arg His Ile Ala Glu Arg Leu Leu Thr Glu Tyr Cys Ile Glu Thr
                565                 570                 575

Gly Ala Pro Asp Gly Ser Phe Leu Val Arg Glu Ser Glu Thr Phe Val
            580                 585                 590

Gly Asp Tyr Thr Leu Ser Phe Trp Arg Asn Gly Lys Val Gln His Cys
        595                 600                 605

Arg Ile His Ser Arg Gln Asp Ala Gly Thr Pro Lys Phe Phe Leu Thr
    610                 615                 620

Asp Asn Leu Val Phe Asp Ser Leu Tyr Asp Leu Ile Thr His Tyr Gln
625                 630                 635                 640

Gln Val Pro Leu Arg Cys Asn Glu Phe Glu Met Arg Leu Ser Glu Pro
                645                 650                 655

Val Pro Gln Thr Asn Ala His Glu Ser Lys Glu Trp Tyr His Ala Ser
            660                 665                 670

Leu Thr Arg Ala Gln Ala Glu His Met Leu Met Arg Val Pro Arg Asp
        675                 680                 685

Gly Ala Phe Leu Val Arg Lys Arg Asn Glu Pro Asn Ser Tyr Ala Ile
    690                 695                 700
```

```
Ser  Phe  Arg  Ala  Glu  Gly  Lys  Ile  Lys  His  Cys  Arg  Val  Gln  Gln  Glu
705                 710                 715                           720

Gly  Gln  Thr  Val  Met  Leu  Gly  Asn  Ser  Glu  Phe  Asp  Ser  Leu  Val  Asp
               725                      730                      735

Leu  Ile  Ser  Tyr  Tyr  Glu  Lys  His  Pro  Leu  Tyr  Arg  Lys  Met  Lys  Leu
               740                      745                      750

Arg  Tyr  Pro  Ile  Asn  Glu  Glu  Ala  Leu  Glu  Lys  Ile  Gly  Thr  Ala  Glu
               755                      760                      765

Pro  Asp  Tyr  Gly  Ala  Leu  Tyr  Glu  Gly  Arg  Asn  Pro  Gly  Phe  Tyr  Val
          770                      775                      780

Glu  Ala  Asn  Pro  Met  Pro  Thr  Phe  Lys  Cys  Ala  Val  Lys  Ala  Leu  Phe
785                      790                      795                      800

Asp  Tyr  Lys  Ala  Gln  Arg  Glu  Asp  Glu  Leu  Thr  Phe  Thr  Lys  Ser  Ala
                    805                      810                      815

Ile  Ile  Gln  Asn  Val  Glu  Lys  Gln  Asp  Gly  Gly  Trp  Trp  Arg  Gly  Asp
                    820                      825                      830

Tyr  Gly  Gly  Lys  Lys  Gln  Leu  Trp  Phe  Pro  Ser  Asn  Tyr  Val  Glu  Glu
          835                      840                      845

Met  Ile  Asn  Pro  Ala  Ile  Leu  Glu  Pro  Glu  Arg  Glu  His  Leu  Asp  Glu
850                      855                      860

Asn  Ser  Pro  Leu  Gly  Asp  Leu  Leu  Arg  Gly  Val  Leu  Asp  Val  Pro  Ala
865                      870                      875                      880

Cys  Gln  Ile  Ala  Ile  Arg  Pro  Glu  Gly  Lys  Asn  Asn  Arg  Leu  Phe  Val
                    885                      890                      895

Phe  Ser  Ile  Ser  Met  Pro  Ser  Val  Ala  Gln  Trp  Ser  Leu  Asp  Val  Ala
               900                      905                      910

Ala  Asp  Ser  Gln  Glu  Glu  Leu  Gln  Asp  Trp  Val  Lys  Lys  Ile  Arg  Glu
               915                      920                      925

Val  Ala  Gln  Thr  Ala  Asp  Ala  Arg  Leu  Thr  Glu  Gly  Lys  Met  Met  Glu
          930                      935                      940

Arg  Arg  Lys  Lys  Ile  Ala  Leu  Glu  Leu  Ser  Glu  Leu  Val  Val  Tyr  Cys
945                      950                      955                      960

Arg  Pro  Val  Pro  Phe  Asp  Glu  Glu  Lys  Ile  Gly  Thr  Glu  Arg  Ala  Cys
                    965                      970                      975

Tyr  Arg  Asp  Met  Ser  Ser  Phe  Pro  Glu  Thr  Lys  Ala  Glu  Lys  Tyr  Val
               980                      985                      990

Asn  Lys  Ala  Lys  Gly  Lys  Lys  Phe  Leu  Gln  Tyr  Asn  Arg  Leu  Gln  Leu
          995                      1000                     1005

Ser  Arg  Ile  Tyr  Pro  Lys  Gly  Gln  Arg  Leu  Asp  Ser  Ser  Asn  Tyr  Asp
     1010                     1015                     1020

Pro  Leu  Pro  Met  Trp  Ile  Cys  Gly  Ser  Gln  Leu  Val  Ala  Leu  Asn  Phe
1025                     1030                     1035                     1040

Gln  Thr  Pro  Asp  Lys  Pro  Met  Gln  Met  Asn  Gln  Ala  Leu  Phe  Met  Ala
                    1045                     1050                     1055

Gly  Gly  His  Cys  Gly  Tyr  Val  Leu  Gln  Pro  Ser  Thr  Met  Arg  Asp  Glu
               1060                     1065                     1070

Ala  Phe  Asp  Pro  Phe  Asp  Lys  Ser  Ser  Leu  Arg  Gly  Leu  Glu  Pro  Cys
     1075                     1080                     1085

Val  Ile  Cys  Ile  Glu  Val  Leu  Gly  Ala  Arg  His  Leu  Pro  Lys  Asn  Gly
     1090                     1095                     1100

Arg  Gly  Ile  Val  Cys  Pro  Phe  Val  Glu  Ile  Glu  Val  Ala  Gly  Ala  Glu
1105                     1110                     1115                     1120

Tyr  Asp  Ser  Thr  Lys  Gln  Lys  Thr  Glu  Phe  Val  Val  Asp  Asn  Gly  Leu
```

|       |       |       |       |       |       |       |       |       |       |       |       |       |       |       |
|---|---|---|---|---|---|---|---|---|---|---|---|---|---|---|
|       |       |       |       | 1125  |       |       |       |       | 1130  |       |       |       |       | 1135  |
| Asn   | Pro   | Val   | Trp   | Pro   | Ala   | Lys   | Pro   | Phe   | His   | Phe   | Gln   | Ile   | Ser   | Asn   | Pro |
|       |       |       |       | 1140  |       |       |       |       | 1145  |       |       |       |       | 1150  |
| Glu   | Phe   | Ala   | Phe   | Leu   | Arg   | Phe   | Val   | Val   | Tyr   | Glu   | Glu   | Asp   | Met   | Phe   | Ser |
|       |       |       |       | 1155  |       |       |       |       | 1160  |       |       |       |       | 1165  |
| Asp   | Gln   | Asn   | Phe   | Leu   | Ala   | Gln   | Ala   | Thr   | Phe   | Pro   | Val   | Lys   | Gly   | Leu   | Lys |
|       |       |       |       | 1170  |       |       |       |       | 1175  |       |       |       |       | 1180  |
| Thr   | Gly   | Tyr   | Arg   | Ala   | Val   | Pro   | Leu   | Lys   | Asn   | Asn   | Tyr   | Ser   | Glu   | Asp   | Leu |
| 1185  |       |       |       |       | 1190  |       |       |       |       | 1195  |       |       |       |       | 1200 |
| Glu   | Leu   | Ala   | Ser   | Leu   | Leu   | Ile   | Lys   | Ile   | Asp   | Ile   | Phe   | Pro   | Ala   | Lys   | Glu |
|       |       |       |       | 1205  |       |       |       |       | 1210  |       |       |       |       | 1215  |
| Asn   | Gly   | Asp   | Leu   | Ser   | Pro   | Phe   | Ser   | Gly   | Thr   | Ser   | Leu   | Arg   | Glu   | Arg   | Ala |
|       |       |       |       | 1220  |       |       |       |       | 1225  |       |       |       |       | 1230  |
| Ser   | Asp   | Ala   | Ser   | Ser   | Gln   | Leu   | Phe   | His   | Val   | Arg   | Ala   | Arg   | Glu   | Gly   | Ser |
|       |       |       |       | 1235  |       |       |       |       | 1240  |       |       |       |       | 1245  |
| Phe   | Glu   | Ala   | Arg   | Tyr   | Gln   | Gln   | Pro   | Phe   | Glu   | Asp   | Phe   | Arg   | Ile   | Ser   | Gln |
|       |       |       |       | 1250  |       |       |       |       | 1255  |       |       |       |       | 1260  |
| Glu   | His   | Leu   | Ala   | Asp   | His   | Phe   | Asp   | Ser   | Arg   | Glu   | Arg   | Arg   | Ala   | Pro   | Arg |
| 1265  |       |       |       |       | 1270  |       |       |       |       | 1275  |       |       |       |       | 1280 |
| Arg   | Thr   | Arg   | Val   | Asn   | Gly   | Asp   | Asn   | Arg   | Leu   |       |       |       |       |       |     |
|       |       |       |       | 1285  |       |       |       |       | 1290  |       |       |       |       |       |     |

( 2 ) INFORMATION FOR SEQ ID NO:3:

( i ) SEQUENCE CHARACTERISTICS:
        ( A ) LENGTH: 3893 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

| | | | | | |
|---|---|---|---|---|---|
| ATGGCGGGCG | CCGCGTCCCC | CTGCGCCAAC | GGCTGCGGGC | CCAGCGCGCC | CTCCGAAGCG | 60 |
| GAGGTGCTGC | ACCTCTGCCG | CAGCCTCGAG | GTGGGCACCG | TCATGACTTT | GTTCTACTCC | 120 |
| AAGAAGTCGC | AGCGGCCAGA | ACGGAAGACC | TTCCAGGTCA | AGTTGGAGAC | GCGCCAGATC | 180 |
| ACATGGAGCC | GCGGTGCGGA | CAAAATCGAG | GGGTCCATCG | ATATCCGAGA | AATCAAGGAG | 240 |
| ATCCGCCCAG | GGAAGACTTC | CCGGGACTTT | GACCGCTACC | AAGAAGACCC | TGCCTTCCGG | 300 |
| CCAGATCAGT | CACACTGTTT | TGTCATCCTC | TATGGAATGG | AATTCCGCCT | GAAGACCCTG | 360 |
| AGCCTGCAAG | CCACATCTGA | GGATGAAGTG | AACATGTGGA | TCAAGGGCTT | AACTTGGCTC | 420 |
| ATGGAAGATA | CGCTGCAGGC | GGCCACACCC | TGCAAATTG | AGAGATGGCT | CCGGAAGCAG | 480 |
| TTCTACTCAG | TGGATCGTAA | CCGAGAGGAT | CGTATATCAG | CCAAGGACCT | GAAGAACATG | 540 |
| CTGTCACAGG | TCAACTACCG | GGTCCCCAAC | ATGCGCTTCC | TCCGAGAGCG | GCTGACGGAC | 600 |
| TTTGAACAGC | GCAGCGGGGA | CATCACCTAT | GGGCAGTTTG | CTCAGCTTTA | CCGCAGCCTC | 660 |
| ATGTACAGCG | CCCAGAAGAC | GATGGACCTT | CCGTTCTTGG | AAACCAACAC | TTTGAGGACT | 720 |
| GGAGAGCGGC | CAGAGCTTTG | CCAGGTGTCC | CTTTCTGAGT | CCAGCAGTT | CCTTCTTGAG | 780 |
| TACCAGGGGG | AGCTGTGGGC | TGTCGACCGG | CTTCAGGTGC | AGGAATTTAT | GCTCAGCTTC | 840 |
| CTTCGAGACC | CCTTGCGAGA | GATTGAGGAG | CCATACTTCT | TCTTGGATGA | GCTTGTCACC | 900 |
| TTTCTGTTCT | CCAAAGAGAA | CAGTGTGTGG | AACTCACAGC | TGGATGCCGT | GTGCCCAGAA | 960 |
| ACCATGAACA | ACCCACTGTC | TCACTATTGG | ATCTCTTCCT | CGCATAATAC | GTATCTGACT | 1020 |
| GGGGACCAGT | TCTCCAGCGA | GTCCTCCCTG | GAAGCCTACG | CTCGCTGCCT | GAGGATGGGC | 1080 |

```
TGTCGCTGCA  TCGAGTTGGA  CTGCTGGGAT  GGGCCAGATG  GGATGCCAGT  CATTTACCAT  1140
GGGCACACCC  TCACCACCAA  GATTAAGTTC  TCAGATGTCC  TGCACACCAT  CAAGGAGCAC  1200
GCGTTCGTAG  CCTCAGAGTA  CCCTGTCATC  CTGTCCATCG  AGGACCACTG  CAGCATTGCC  1260
CAGCAGAGGA  ACATGGCCCA  GCACTTCAGG  AAGGTGCTCG  GTGACACGCT  CCTCACCAAG  1320
CCCGTGGACA  TTGCCGCTGA  TGGGCTCCCT  TCTCCCAACC  AGCTCAAGAG  GAAGATCCTG  1380
ATTAAGCATA  AGAAGCTGGC  TGAGGGCAGT  GCCTATGAGG  AGGTGCCTAC  CTCTGTGATG  1440
TACTCTGAGA  ATGACATCAG  TAACTCCATC  AAGAATGGTA  TCCTCTACTT  GGAGGACCCC  1500
GTGAATCATG  AGTGGTACCC  CCACTACTTT  GTTCTGACTA  GCAGCAAGAT  CTACTACTCT  1560
GAGGAGACCA  GCAGTGACCA  GGGAAATGAG  GATGAAGAGG  AGCCGAAGGA  GGCCAGTGGC  1620
AGCACAGAGC  TGCACTCGAG  CGAGAAGTGG  TTCCACGGGA  AGCTCGGGGC  TGGGCGCGAC  1680
GGGCGGCACA  TTGCTGAGCG  CCTGCTCACC  GAGTACTGCA  TAGAGACTGG  GGCTCCCGAT  1740
GGCTCCTTCC  TAGTGCGAGA  AAGTGAGACC  TTCGTGGGGG  ACTACACGCT  GTCTTTTTGG  1800
CGGAATGGGA  AAGTCCAGCA  CTGCCGTATC  CACTCCCGGC  AGGATGCTGG  GACTCCTAAG  1860
TTCTTCTTGA  CAGATAACCT  TGTCTTTGAC  TCTCTCTATG  ACCTCATCAC  ACATTATCAG  1920
CAAGTGCCCC  TGCGCTGCAA  TGAGTTTGAG  ATGCGCCTTT  CAGAGCCTGT  TCCACAGACG  1980
AATGCCCATG  AGAGCAAAGA  GTGGTACCAC  GCAAGCCTGA  CTAGAGCTCA  GGCTGAACAC  2040
ATGCTGATGC  GAGTACCCCG  TGATGGGGCC  TTCCTGGTGC  GGAAGCGCAA  CGAGCCCAAC  2100
TCCTATGCCA  TCTCTTTCCG  GGCTGAGGGA  AAGATCAAGC  ACTGCCGAGT  ACAGCAGGAA  2160
GGCCAGACTG  TGATGCTGGG  GAACTCTGAG  TTTGACAGCC  TGGTCGACCT  CATCAGCTAC  2220
TATGAGAAGC  ATCCCCTGTA  CCGCAAAATG  AAACTGCGCT  ACCCCATCAA  CGAGGAGGCG  2280
CTGGAGAAGA  TTGGGACAGC  TGAACCCGAT  TATGGGGCAC  TGTATGAGGG  CCGCAACCCT  2340
GGTTTCTATG  TGGAGGCCAA  CCCTATGCCA  ACTTTCAAGT  GTGCAGTAAA  AGCTCTCTTC  2400
GACTACAAGG  CCCAGAGAGA  GGATGAGCTG  ACTTTTACCA  AGAGCGCCAT  CATCCAGAAT  2460
GTGGAAAAGC  AAGATGGTGG  CTGGTGGCGT  GGGGACTATG  GTGGGAAGAA  GCAGCTGTGG  2520
TTCCCCTCAA  ACTATGTGGA  AGAGATGATC  AATCCAGCAA  TCCTAGAGCC  GGAGAGGGAG  2580
CATCTGGATG  AGAACAGCCC  ACTGGGGGAC  TTGCTGCGAG  GGTCTTAGA  TGTGCCAGCC  2640
TGCCAGATCG  CCATTCGTCC  TGAGGGCAAA  AACAACCGGC  TCTTCGTCTT  CTCCATCAGC  2700
ATGCCGTCAG  TGGCTCAGTG  GTCCCTAGAC  GTTGCCGCTG  ACTCACAGGA  GGAGTTGCAG  2760
GACTGGGTGA  AAAAGATCCG  TGAAGTTGCC  CAGACTGCAG  ATGCCAGGCT  TACTGAGGGG  2820
AAGATGATGG  AGCGGCGGAA  GAAGATCGCC  TTGGAGCTCT  CCGAGCTCGT  GGTCTACTGC  2880
CGGCCTGTTC  CCTTTGACGA  AGAGAAGATT  GGCACAGAAC  GCGCTTGTTA  CCGGGACATG  2940
TCCTCCTTTC  CGGAAACCAA  GGCTGAGAAG  TATGTGAACA  AGGCCAAAGG  CAAGAAGTTC  3000
CTCCAGTACA  ACCGGCTGCA  GCTCTCTCGC  ATCTACCCTA  AGGGTCAGAG  GCTGGACTCC  3060
TCCAATTATG  ACCCTCTGCC  CATGTGGATC  TGTGGCAGCC  AGCTTGTAGC  TCTCAATTTT  3120
CAGACCCCAG  ACAAGCCTAT  GCAGATGAAC  CAGGCCCTCT  TCATGGCTGG  TGGACACTGT  3180
GGCTATGTGC  TGCAGCCAAG  CACCATGAGA  GATGAAGCCT  TTGACCCCTT  TGATAAGAGC  3240
AGTCTCCGAG  GTCTGGAGCC  CTGTGTCATT  TGCATTGAGG  TGCTGGGGGC  CAGGCATCTG  3300
CCGAAGAATG  GCCGGGGTAT  TGTGTGTCCT  TTCGTGGAGA  TTGAAGTGGC  TGGGGCAGAG  3360
TACGACAGCA  CCAAGCAGAA  GACAGAGTTT  GTAGTGGACA  ATGGACTGAA  CCCTGTGTGG  3420
CCTGCAAAGC  CCTTCCACTT  CCAGATCAGT  AACCCAGAGT  TTGCCTTTCT  GCGCTTTGTG  3480
```

| | | | | | |
|---|---|---|---|---|---|
| GTGTATGAGG | AAGACATGTT | TAGTGACCAG | AACTTCTTGG | CTCAGGCTAC | TTTCCCAGTA | 3540
| AAAGGCCTGA | AGACAGGATA | CAGAGCAGTG | CCTTTGAAGA | ACAACTACAG | TGAAGACCTG | 3600
| GAGTTGGCCT | CCCTGCTCAT | CAAGATTGAC | ATTTCCCTG | CTAAGGAGAA | TGGTGACCTC | 3660
| AGCCCTTTCA | GTGGTACATC | CCTAAGGGAA | CGGGCCTCAG | ATGCCTCCAG | CCAGCTGTTC | 3720
| CATGTCCGGG | CCCGGGAAGG | GTCCTTTGAA | GCCAGATACC | AGCAGCCATT | TGAAGACTTC | 3780
| CGCATCTCGC | AGGAGCATCT | CGCAGACCAT | TTTGACAGTC | GGGAACGAAG | GGCCCCAAGA | 3840
| AGGACTCGGG | TCAATGGAGA | CAACCGCCTC | GAAGAATTTT | AGTCTAGAAG | CTT | 3893

( 2 ) INFORMATION FOR SEQ ID NO:4:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

CCCGGGCATA TGGATCCATT GGAGGATGAT TAAATGGCGG GCGCCGCGTC C    51

( 2 ) INFORMATION FOR SEQ ID NO:5:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

CTGCTTCCGG AGCCACCTCT C    21

( 2 ) INFORMATION FOR SEQ ID NO:6:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:6:

TCGCCATTCG TCCTGAGGGC    20

( 2 ) INFORMATION FOR SEQ ID NO:7:

( i ) SEQUENCE CHARACTERISTICS:
        ( A ) LENGTH: 62 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:7:

GGGCCCAAGC TTCTAGACTA AAATTCTTCG AGGCGGTTGT CTCCATTGAC CCGAGTTCGT    60

CG    62

( 2 ) INFORMATION FOR SEQ ID NO:8:

( i ) SEQUENCE CHARACTERISTICS:
   ( A ) LENGTH: 26 base pairs
   ( B ) TYPE: nucleic acid
   ( C ) STRANDEDNESS: single
   ( D ) TOPOLOGY: linear ( i i ) MOLECULE TYPE: cDNA ( x i ) SEQUENCE DESCRIPTION: SEQ ID NO:8:

GATGATGGAG CGGCGGAAGA AGATCG                          26

( 2 ) INFORMATION FOR SEQ ID NO:9:

( i ) SEQUENCE CHARACTERISTICS:
      ( A ) LENGTH: 26 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:9:

CGATCTTCTT CCGCCGCTCC ATCATC                          26